United States Patent
Takakura et al.

(10) Patent No.: US 10,578,584 B2
(45) Date of Patent: Mar. 3, 2020

(54) CALIBRATION DEVICE FOR NON-DESTRUCTIVE INSPECTION/MEASUREMENT SYSTEM AND NON-DESTRUCTIVE INSPECTION/MEASUREMENT METHOD

(71) Applicant: DAINICHI Machine and Engineering Co., Ltd., Yokohama-shi (JP)

(72) Inventors: Kazuma Takakura, Yokohama (JP); Gijun Idei, Yokohama (JP); Masao Kaizuka, Yokohama (JP)

(73) Assignee: DAINICHI Machine and Engineering Co., Ltd., Yokohama-shi (JP)

( * ) Notice: Subject to any disclaimer, the term of this patent is extended or adjusted under 35 U.S.C. 154(b) by 212 days.

(21) Appl. No.: 15/724,672

(22) Filed: Oct. 4, 2017

(65) Prior Publication Data

US 2018/0095056 A1   Apr. 5, 2018

(30) Foreign Application Priority Data

Oct. 5, 2016 (JP) .................................. 2016-197270

(51) Int. Cl.
G01N 27/90 (2006.01)

(52) U.S. Cl.
CPC ..... *G01N 27/9086* (2013.01); *G01N 27/9033* (2013.01)

(58) Field of Classification Search
CPC ....................... G01N 27/9086; G01N 27/9033
USPC .. 324/600, 601, 713, 500–521, 522, 764.01, 324/718, 115–124, 76.11, 200, 202, 324/207.13–245, 529–530; 316/719, 720, 316/736, 748, 761; 320/109–126, 160
See application file for complete search history.

(56) References Cited

U.S. PATENT DOCUMENTS

| | | | |
|---|---|---|---|
| 2008/0074109 A1 | 3/2008 | Tsukada et al. | |
| 2010/0271012 A1* | 10/2010 | Patterson | ............... G01B 7/004 324/207.15 |

(Continued)

FOREIGN PATENT DOCUMENTS

| | | |
|---|---|---|
| JP | 3266128 | 3/2002 |
| JP | 3753499 | 3/2006 |

(Continued)

*Primary Examiner* — Melissa J Koval
*Assistant Examiner* — Trung Nguyen
(74) *Attorney, Agent, or Firm* — Oblon, McClelland, Maier & Neustadt, L.L.P.

(57) ABSTRACT

A calibration device for a non-destructive inspection/measurement system is provided, including an excitation coil; a detection coil; and a computer that applies a sinusoidal signal or a combined signal including multiple sinusoids having mutually different frequencies to the excitation coil in order to excite a pipe body, and that detects changes in the output voltage of the detection coil. The calibration device calibrates the detection results in the computer by entering, as variables in simultaneous equations, the amplitudes and phase differences of the output voltage of the detection coil at multiple calibration points of known thickness on the pipe body. The calibration device performs calibrations by using multiple different calibration conditions at each of the calibration points, and entering, into the simultaneous equations, the amplitudes and phase differences of the output voltage of the detection coil for each of the calibration conditions.

17 Claims, 18 Drawing Sheets

(56) References Cited

U.S. PATENT DOCUMENTS

2014/0055130 A1    2/2014  Nakamura et al.
2014/0247048 A1*   9/2014  Cochrane ............. G01R 33/385
                                                        324/322

FOREIGN PATENT DOCUMENTS

| JP | 3896489 | 3/2007 |
| JP | 2010-048552 | 3/2010 |
| JP | 2010-054352 | 3/2010 |
| JP | 4756409 | 8/2011 |
| JP | 2015-87168 | 5/2015 |
| JP | 2016-8931 | 1/2016 |

\* cited by examiner

[FIG.1]
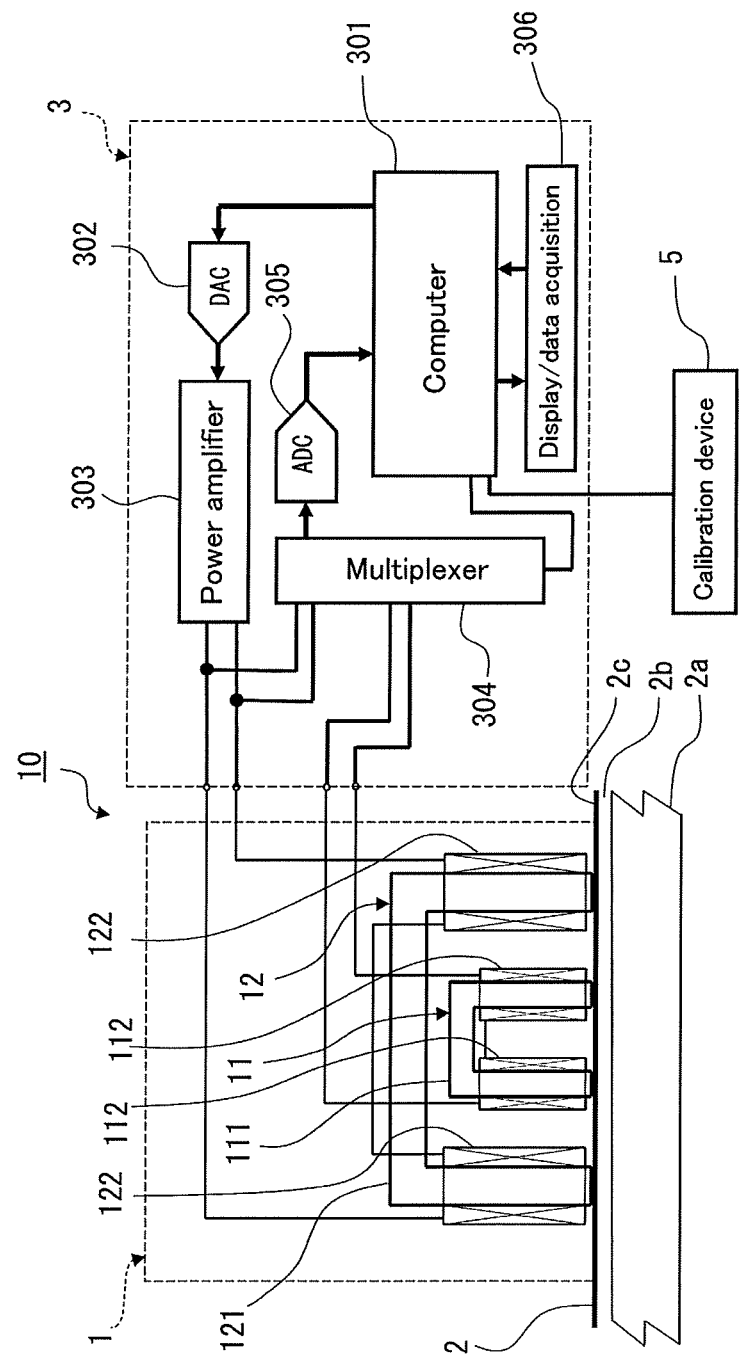

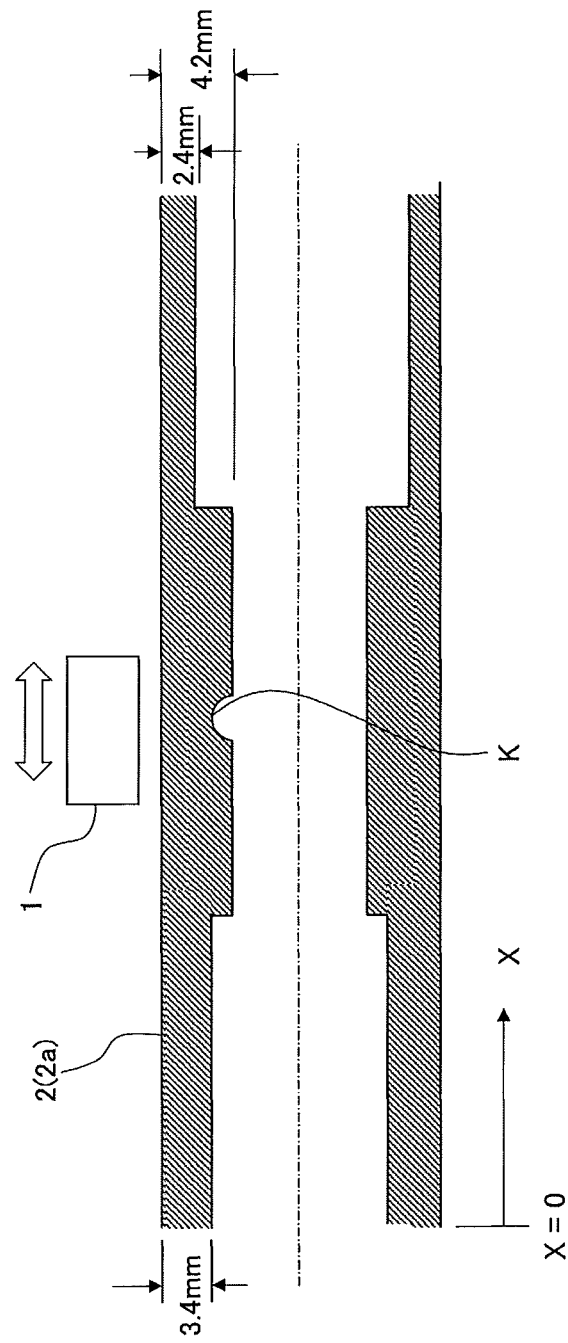

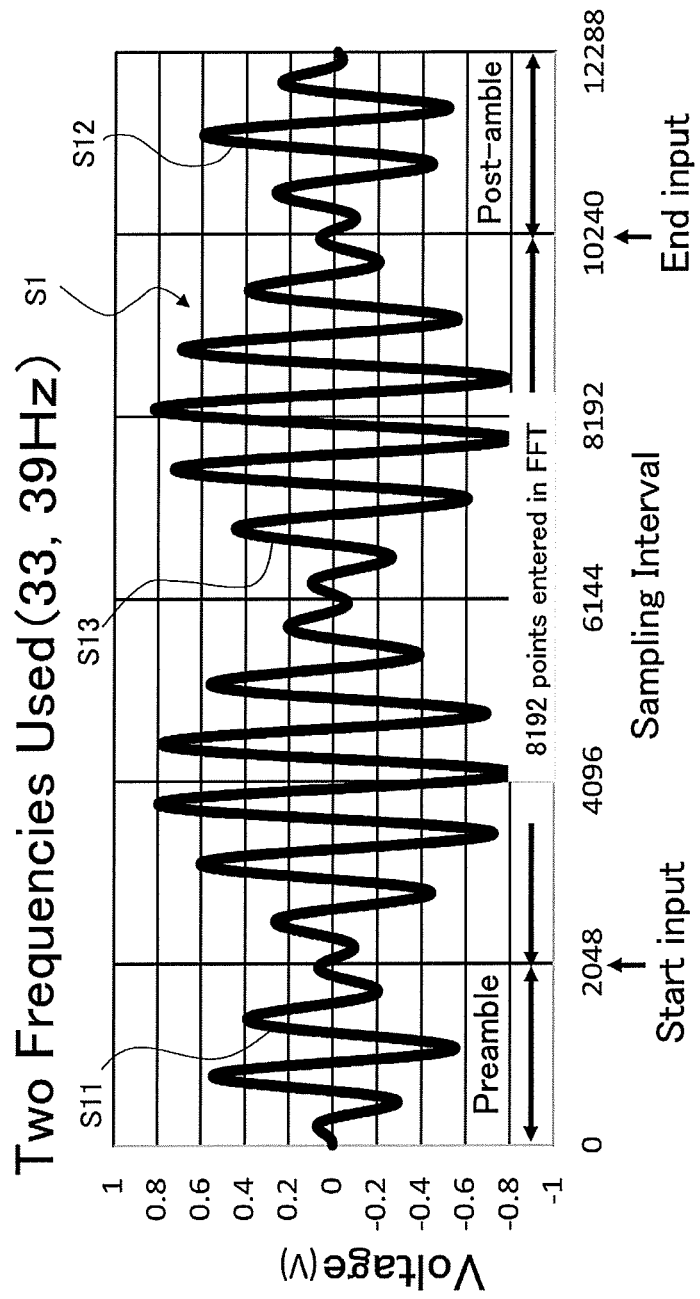
[FIG. 3]

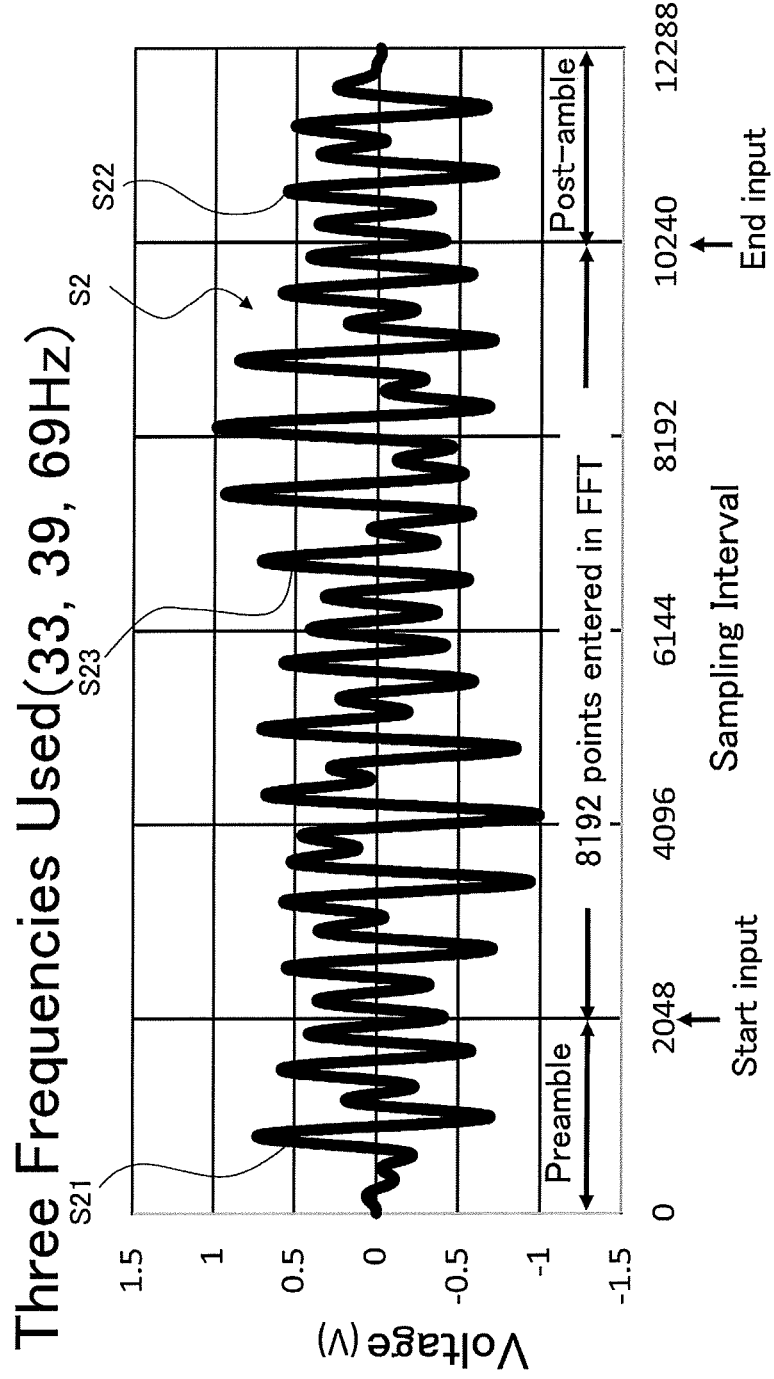
[FIG. 4]

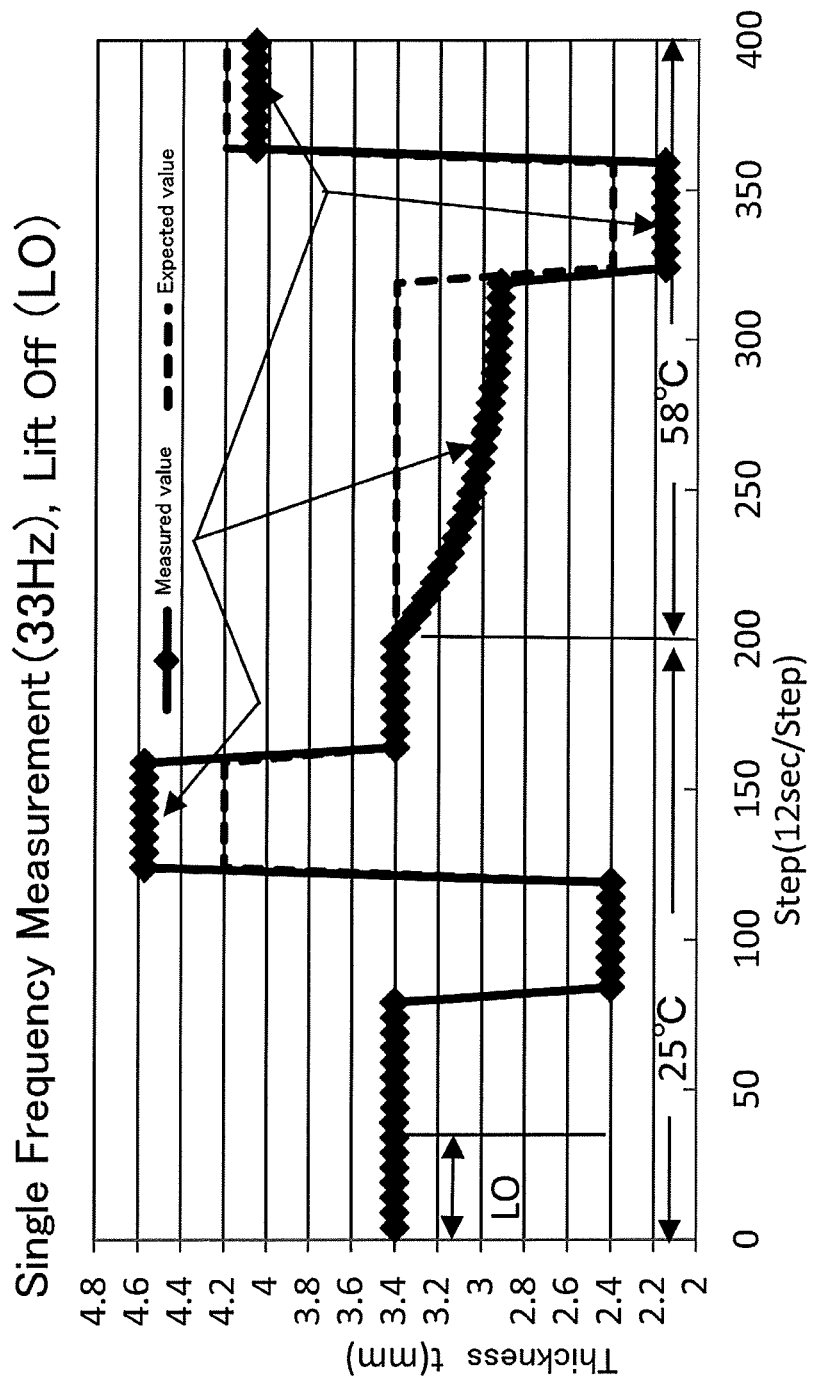

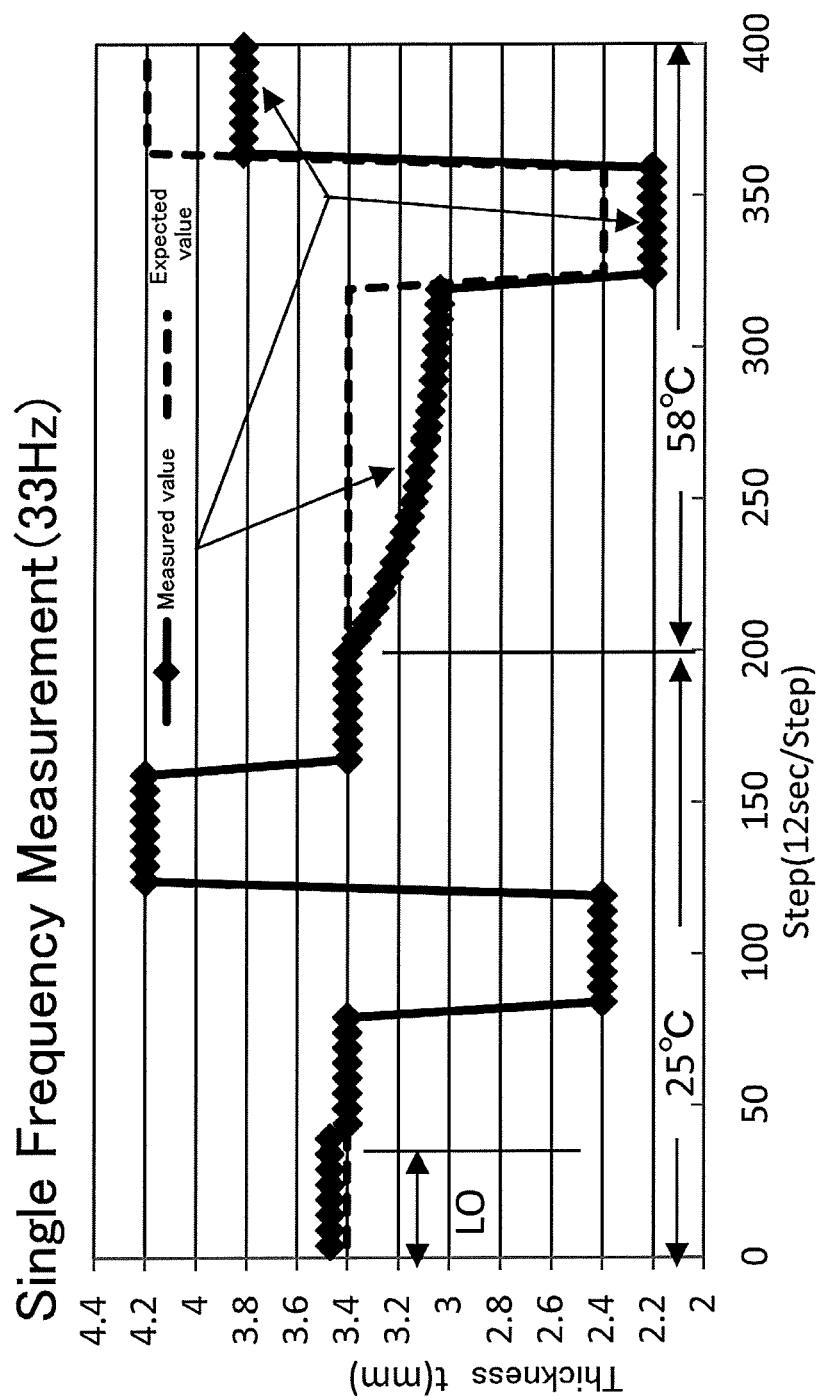

[FIG. 7]
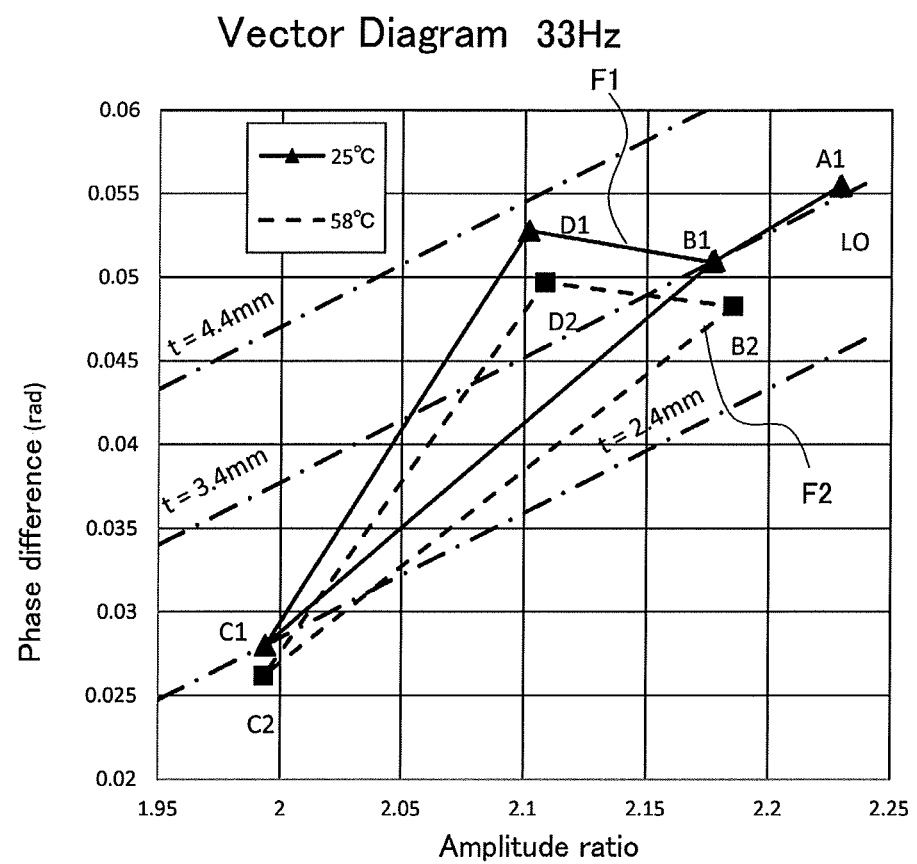

[FIG. 8]
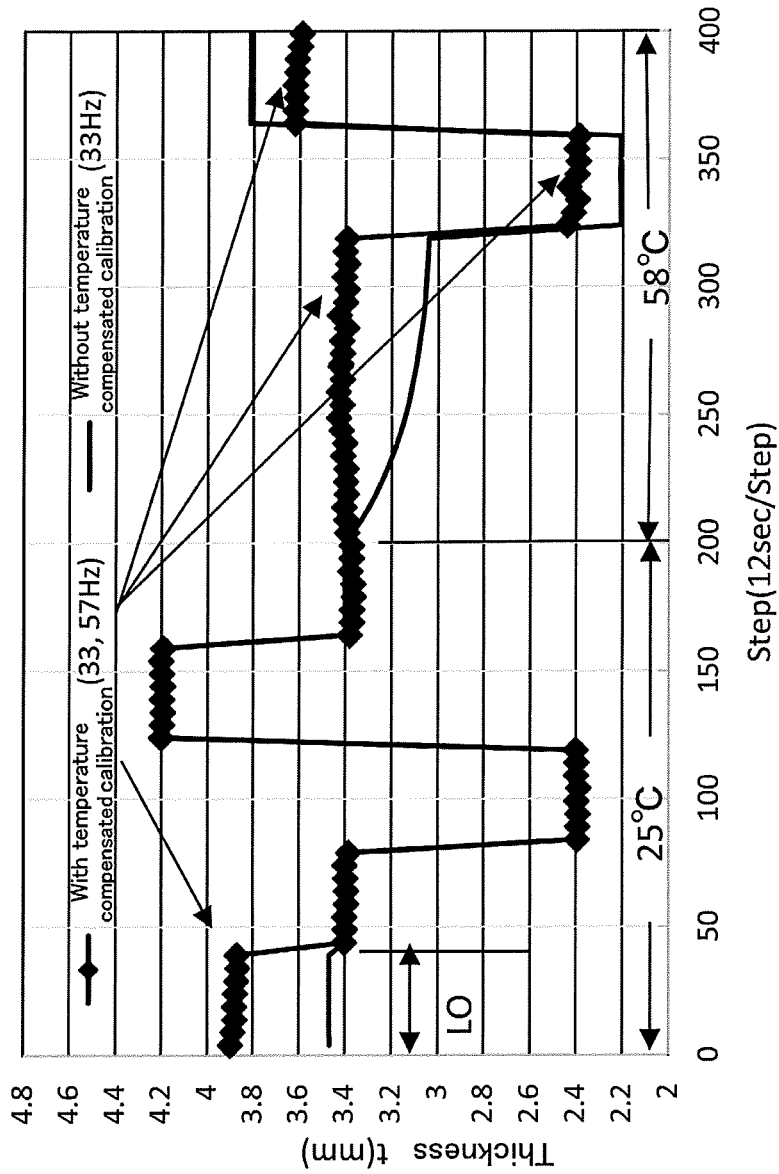

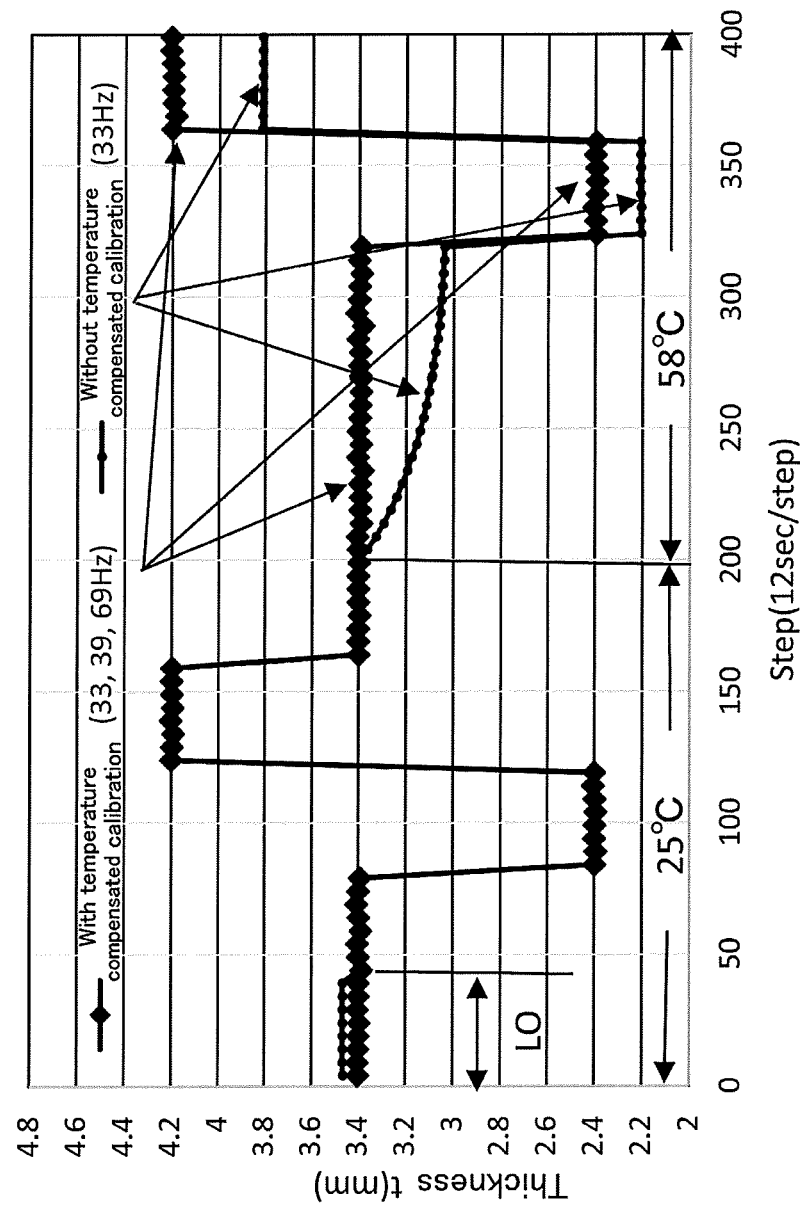
[FIG. 9]

[FIG. 10]
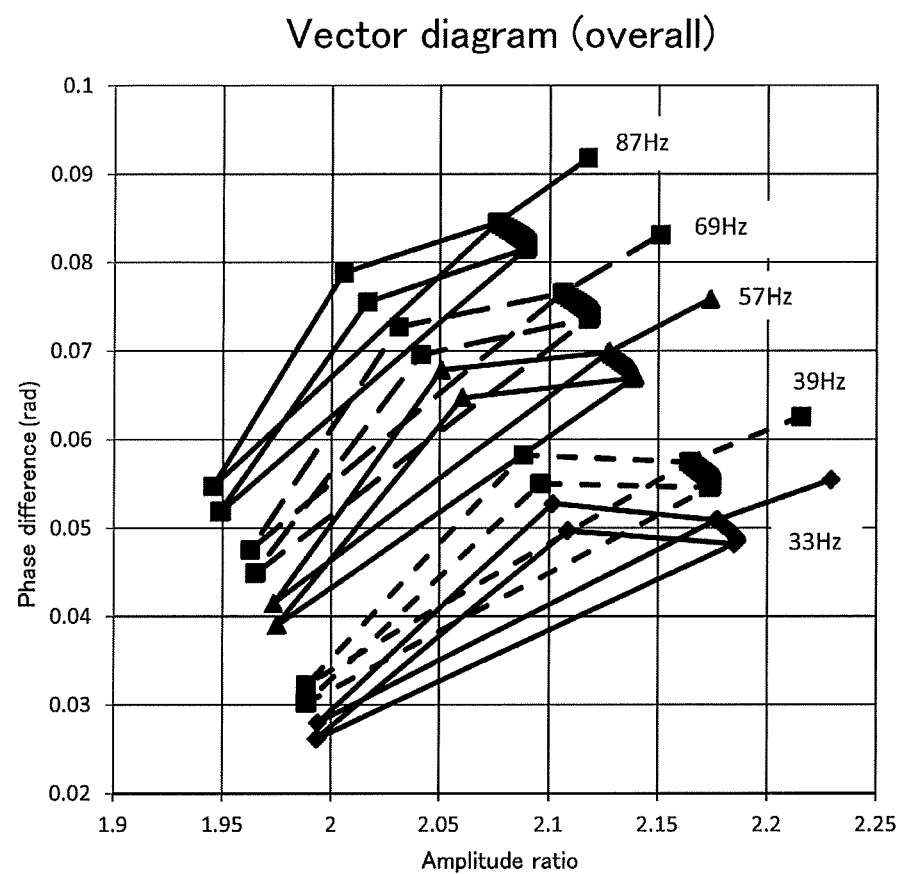

[FIG. 11]
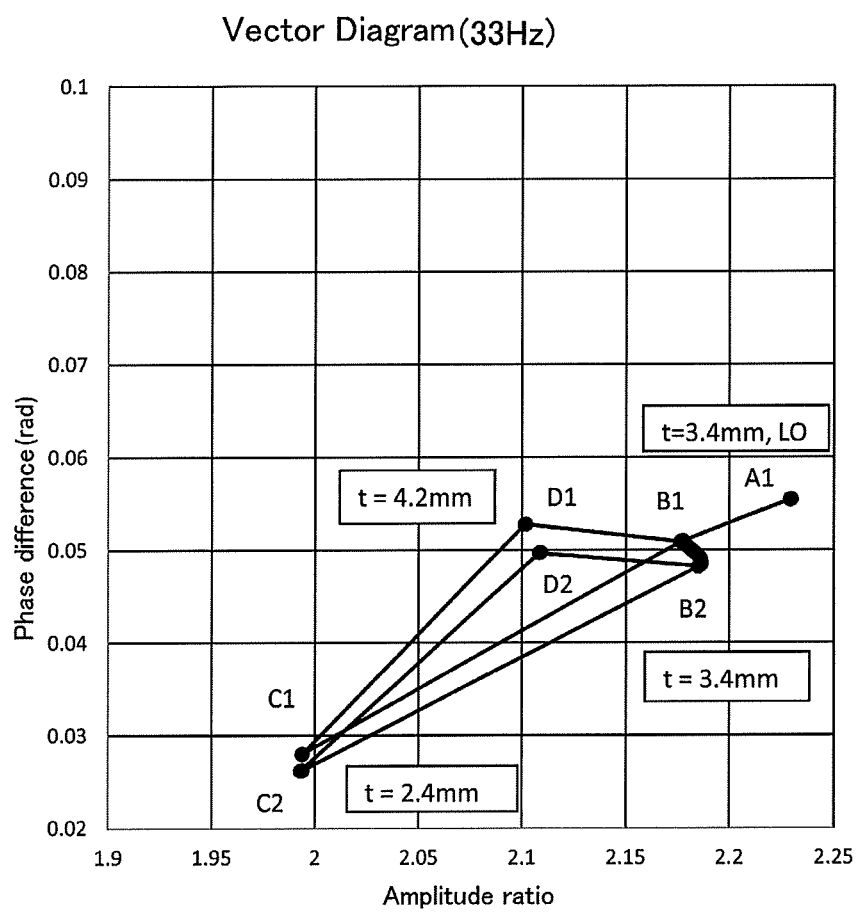

[FIG. 12]
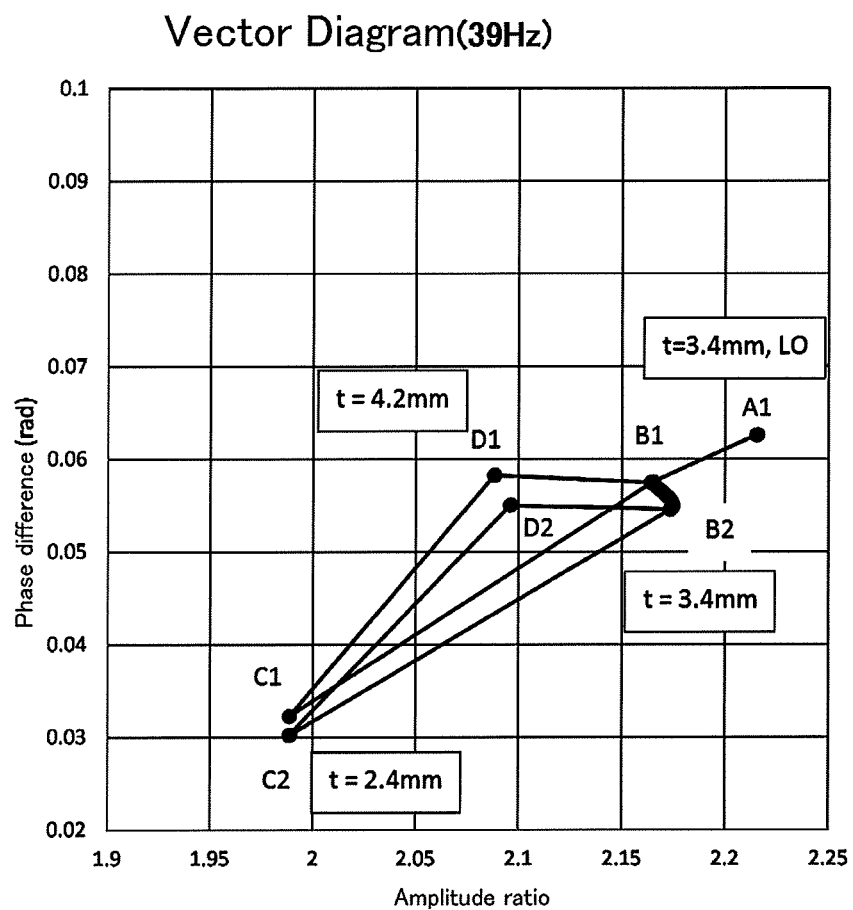

[FIG. 13]
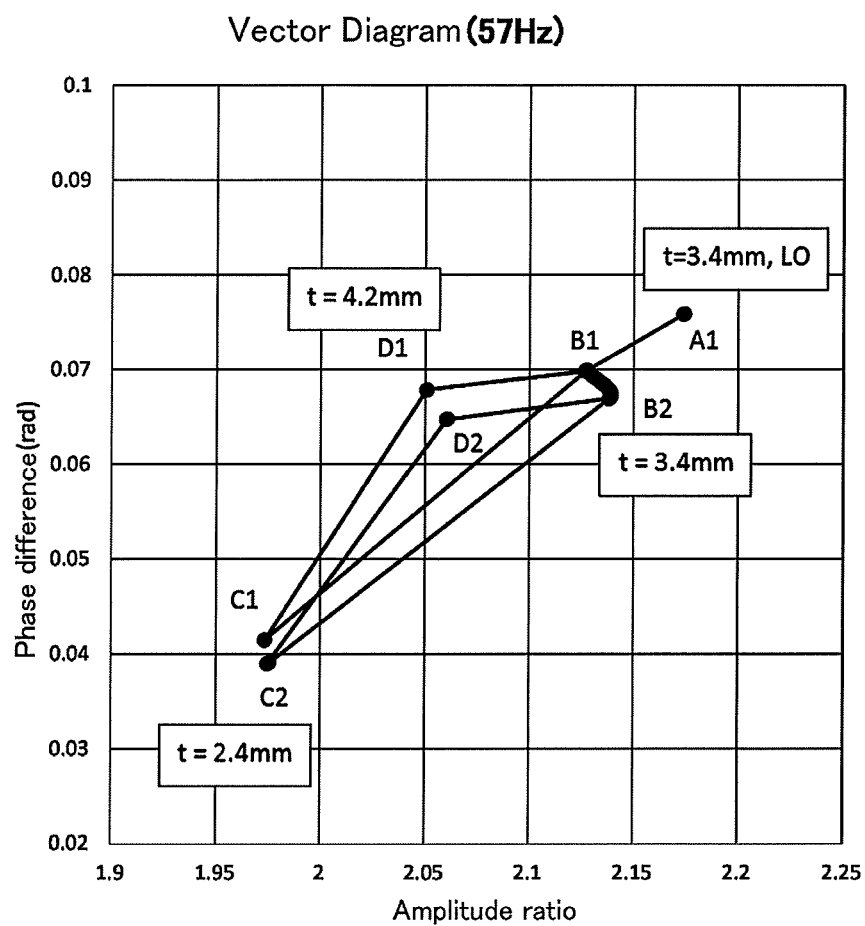

[FIG. 14]
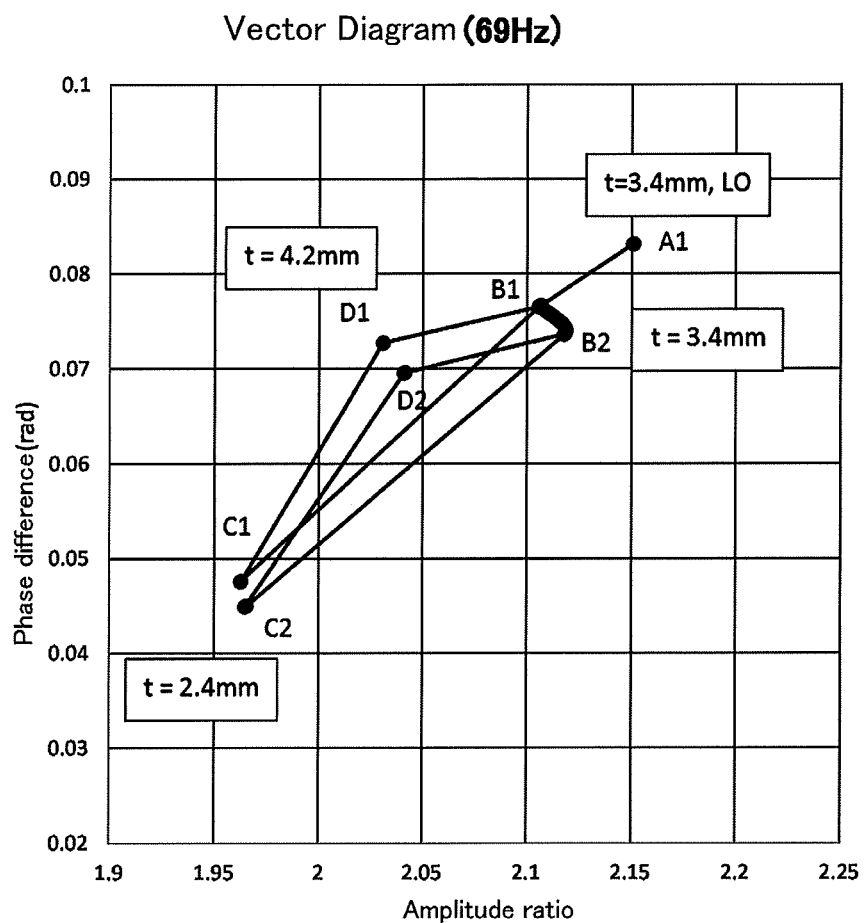

[FIG. 15]
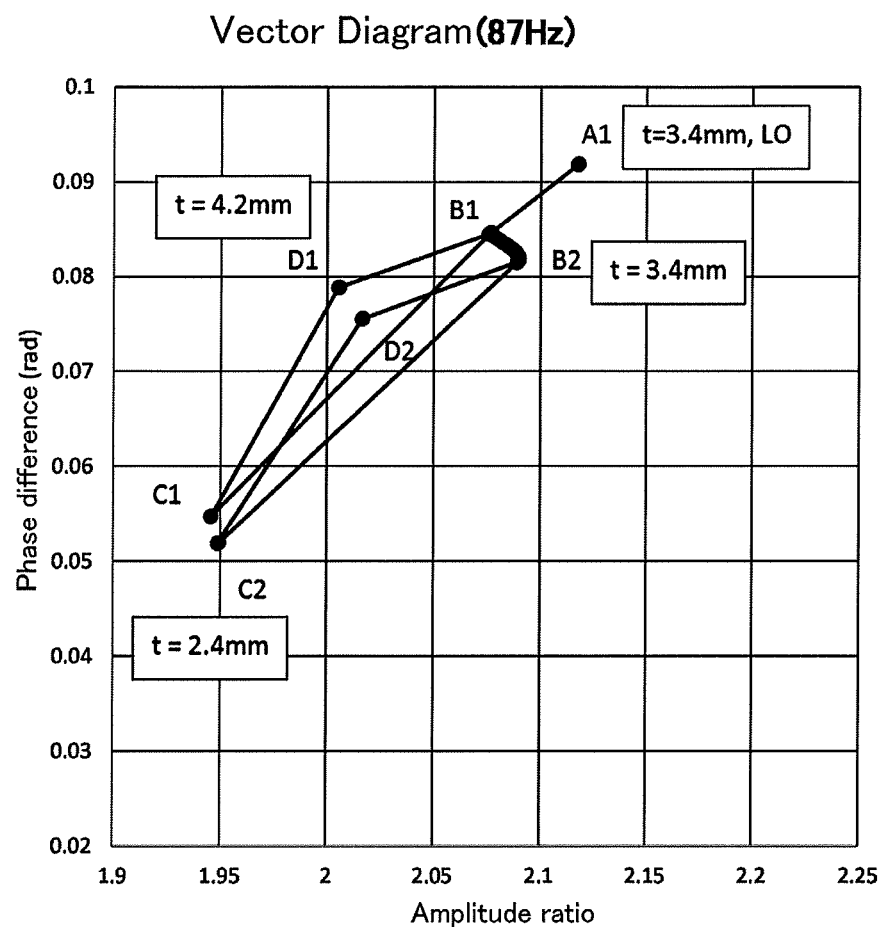

[FIG. 16]
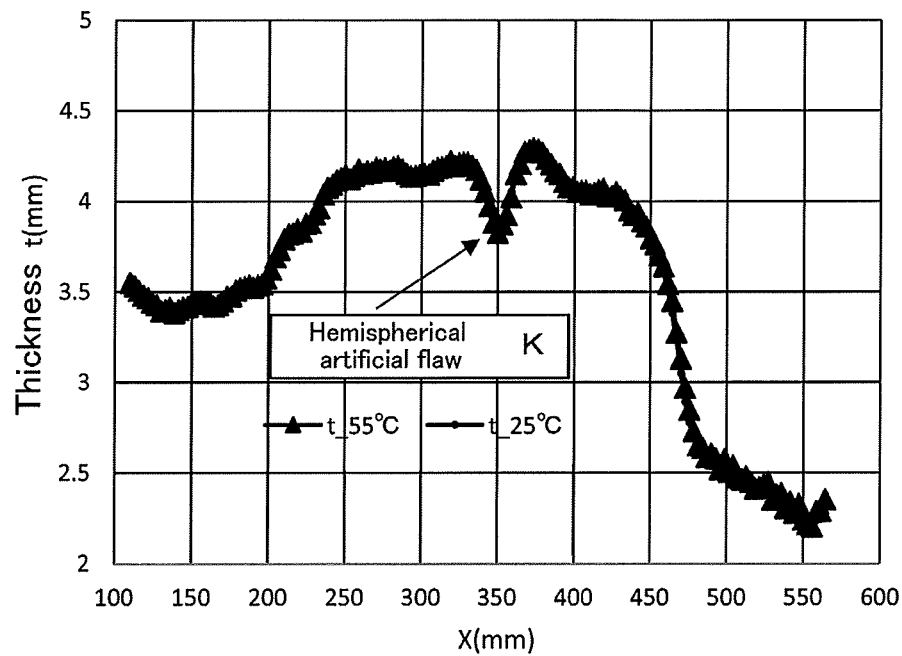
[FIG. 17]
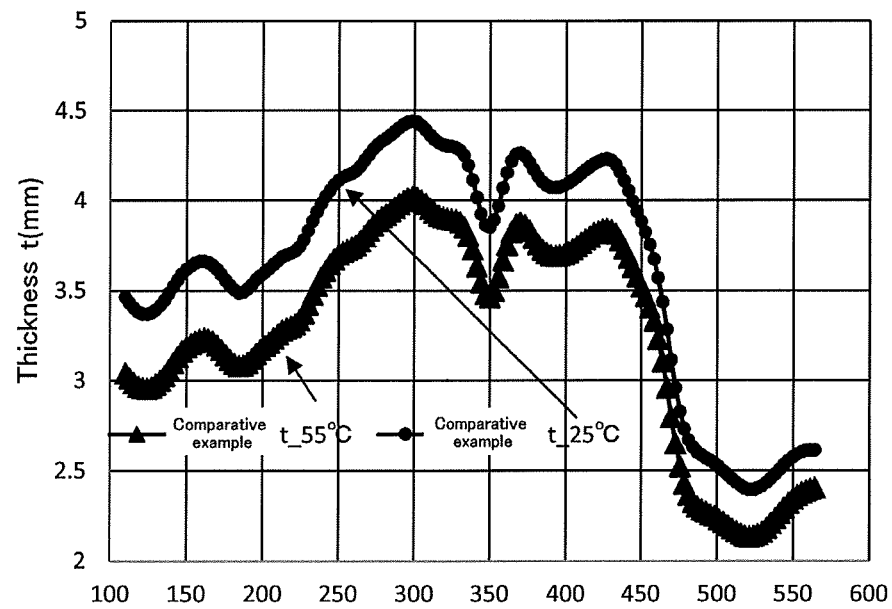

[FIG. 18]
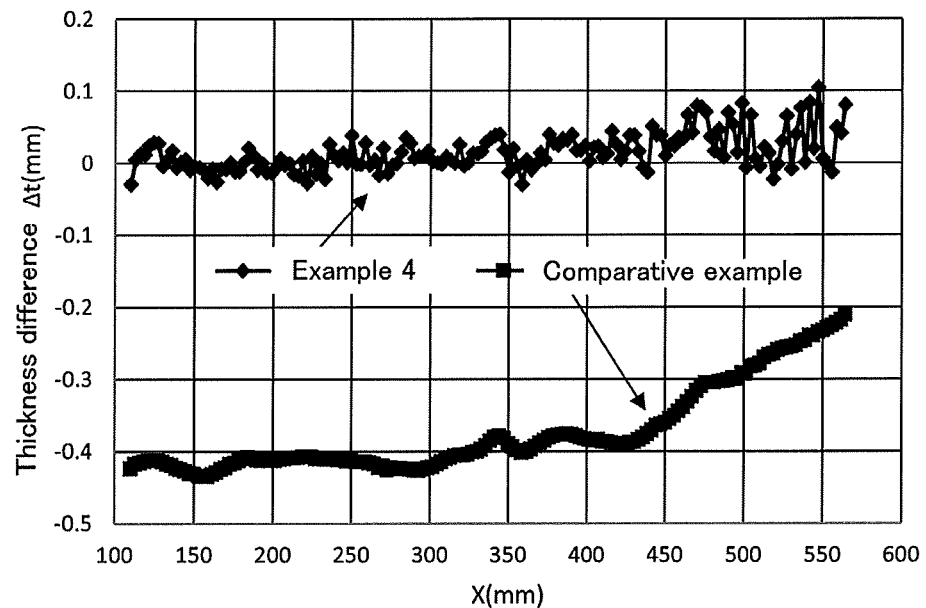
[FIG. 19]
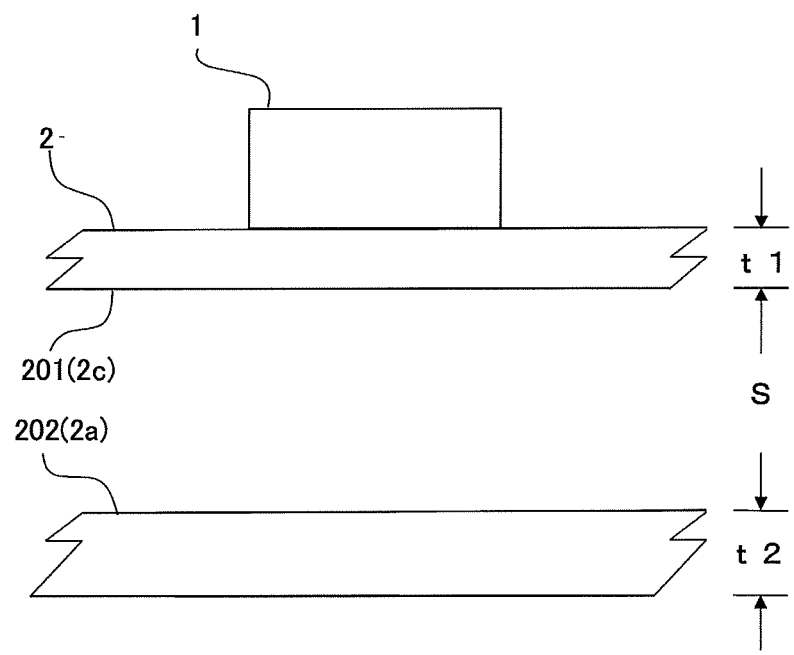

[FIG. 20]
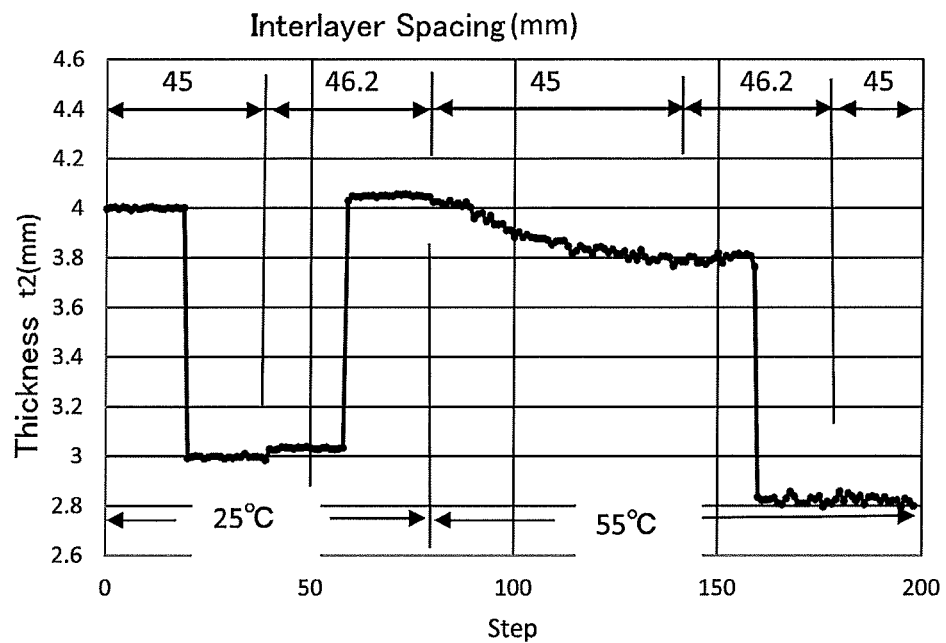
[FIG. 21]
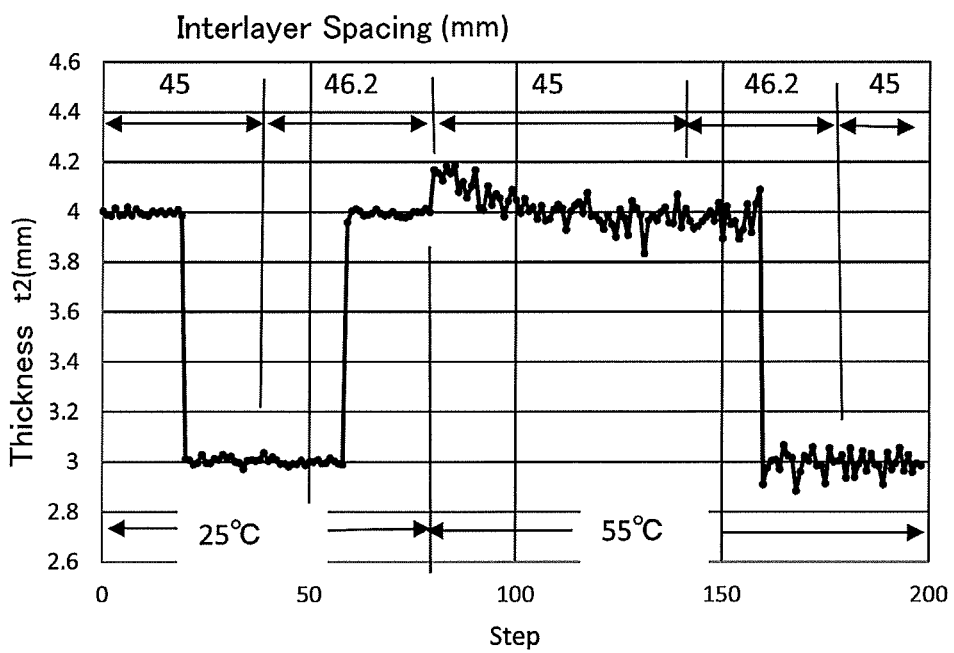

CALIBRATION DEVICE FOR NON-DESTRUCTIVE INSPECTION/MEASUREMENT SYSTEM AND NON-DESTRUCTIVE INSPECTION/MEASUREMENT METHOD

TECHNICAL FIELD

The present invention relates to a calibration device for a non-destructive inspection/measurement system that performs non-destructive inspection and measurement of test objects by making use of electromagnetic induction, and a non-destructive inspection/measurement method.

BACKGROUND ART

As shown in Patent Documents 1-6, among eddy-current flaw detection devices that make use of electromagnetic induction, devices that are calibrated by analysis circuits or the like provided with a sine wave generator, a drive circuit for driving an excitation coil, a sensor comprising an excitation coil and a detection coil, an amplification circuit for amplifying the output of the detection coil, and a synchronized wave detection circuit have been proposed and used.

RELATED ART DOCUMENTS

Patent Documents

[Patent Document 1] JP 3753499 B
[Patent Document 2] JP 3266128 B
[Patent Document 3] JP 2010-48552 A
[Patent Document 4] JP 3896489 B
[Patent Document 5] JP 2010-54352 A
[Patent Document 6] JP 4756409 B

SUMMARY OF THE INVENTION

However, in conventional eddy-current flaw detection devices as mentioned above, the measurement precision decreases if the temperature of the test object changes.

Additionally, if the thickness varies depending on the location on a single test object, there may be cases in which the thickness of the test object cannot be precisely measured at each of multiple locations of different thickness.

Furthermore, in some cases, the test object comprises, for example, a tubular test object body and an outer covering that is provided on the outside of the tubular test object body and that covers the outside of the test object, and the thickness of the test object body is to be measured. In such cases, if the distance between the test object and an adjacent body (outer covering) provided adjacent to the test body varies, then the measurement precision may be affected.

Therefore, a purpose of the present invention is to provide a calibration device for a non-destructive inspection/measurement system and a non-destructive inspection/measurement method that are able to maintain high measurement precision regardless of various condition changes in the test object.

Means for Solving the Problems

The present invention employs the following means for solving the above-mentioned problems.

In other words, the calibration device for a non-destructive inspection/measurement system of the present invention comprises an excitation coil that faces a test object body and that excites the test object body, a detection coil that is provided so as to face the test object body and that outputs a voltage in accordance with a magnetic field change generated in the test object body when the test object body is excited by the excitation coil, and a detection processing unit that applies, to the excitation coil for exciting the test object body, a sinusoidal signal or a combined signal comprising a plurality of sinusoids of mutually different frequencies, and that detects the output voltage of the detection coil; wherein the calibration device comprises a calibration processing unit that calibrates detection results in the detection processing unit by entering, as variables in simultaneous equation, amplitudes and phase differences of the output voltage of the detection coil at a plurality of calibration points of known thickness on the test object body; and the calibration processing unit performs calibrations by using multiple different calibration conditions at each of the calibration points, and entering, into the simultaneous equations, the amplitudes and phase differences of the output of the detection coil for each of the calibration conditions.

Due to such a configuration, by performing calibrations of the test object body using multiple different calibration conditions at each of a plurality of calibration points of known thickness on a test object body, it is possible to perform calibrations at a high precision in accordance with various condition changes in the test object.

The calibration processing unit may be configured to calibrate detection results in the detection processing unit by entering, as variables in simultaneous equations, the amplitudes and phase differences of the output voltage of the detection coil for each of two or more mutually different temperature conditions.

Due to such a configuration, by performing calibrations using multiple different temperature conditions, it is possible to maintain the measurement precision at a high precision level even if the temperature conditions vary when measuring the test object body.

The calibration processing unit may be configured to calibrate detection results in the detection processing unit by entering, as variables in simultaneous equations, the amplitudes and phase differences of the output voltage of the detection coil for respective cases in which at least one of a thickness of the test object body and a spacing between the test object body and an adjacent body provided so as to be spaced with respect to the test object body is changed between multiple values.

Due to such a configuration, by performing calibrations using multiple different thicknesses of the test object body and spacings between the test object and the adjacent body, it is possible to maintain the measurement precision at a high precision level even if the thickness of the test object body or the spacing between the test object and the adjacent body varies when measuring the test object body.

The calibration processing unit may be configured to calibrate detection results in the detection processing unit by entering, as variables in simultaneous equations, the amplitudes and phase differences of the output voltage of the detection coil for each of three or more locations, having mutually different thicknesses, on the test object body.

Due to such a configuration, by performing calibrations at three or more locations having mutually different thicknesses on the test object body, it is possible to maintain the measurement precision at a high precision level at each part having a different thickness when measuring the test object body.

The calibration processing unit may be configured to use multiple different frequencies for the sinusoidal signals applied to the excitation coil, and to calibrate detection results in the detection processing unit by entering as variables in simultaneous equations, the amplitudes and phase differences of the output voltage of the detection coil at each frequency.

Due to such a configuration, by performing calibrations by using multiple different frequencies for the sinusoidal signals applied to the excitation coil, it is possible to maintain in the measurement precision at a high precision level.

The calibration processing unit may be configured to apply a combined signal comprising multiple sinusoids of mutually different frequencies to the excitation coil, and to calibrate detection results in the detection processing unit by entering, as variables in simultaneous equations, the amplitudes and phase differences of the output voltage of the detection coil at each frequency.

Due to such a configuration, by performing calibrations by applying combined signals comprising multiple sinusoids having mutually different frequencies to the excitation coil, it is possible to maintain the measurement precision at a high precision level.

The calibration processing unit may be configured to apply, to the excitation coil, as the sinusoidal signal or the combined signal, a burst signal having a leading section in which the amplitude gradually rises, a trailing section in which the amplitude gradually falls, and a measurement signal section, between the leading section and the trailing section, that is in the steady state and that is for data acquisition.

The calibration processing unit may be configured to use, as the simultaneous equations, multivariable simultaneous equations having five or more variables.

Additionally, the non-destructive inspection/measurement method of the present invention is a non-destructive inspection/measurement method using the calibration device for a non-destructive inspection/measurement system as described above, involving, in the non-destructive inspection/measurement system, exciting the test object body by applying, to the excitation coil, the sinusoidal signal or the combined signal comprising multiple sinusoids having mutually different frequencies, with the excitation coil facing the test object body, and detecting the amplitude and the phase of the output voltage of the detection coil in accordance with magnetic field changes including magnetic flux due to eddy currents generated in the test object body, and the calibration processing unit calibrating the detection results in the detection processing unit by using multiple different calibration conditions, and entering, as variables in the simultaneous equations, the amplitudes and phase differences of the output voltage of the detection coil for each of the calibration conditions.

Effects of the Invention

According to the present invention, it is possible to raise the measurement precision regardless of various condition changes in a test object, by performing calibrations using multiple different conditions.

BRIEF DESCRIPTION OF THE DRAWINGS

FIG. 1 A diagram illustrating the structure of a non-destructive inspection/measurement system and a calibration device according to an embodiment of the present invention.

FIG. 2 A diagram illustrating an example of a test object that is to be measured in the non-destructive inspection/measurement system according to an embodiment of the present invention.

FIG. 3 A diagram illustrating a specific wave form of a combined signal used for measurement in Example 1 in which calibrations were performed by a calibration device in a non-destructive inspection/measurement system according to the first embodiment.

FIG. 4 A diagram illustrating a different specific waveform of a combined signal used for measurement in Example 1 in which calibrations were performed by a calibration device in a non-destructive inspection/measurement system according to the first embodiment.

FIG. 5 A graph illustrating measurement results in a comparative example in which calibrations were performed by a conventional technique.

FIG. 6 A graph illustrating the measurement results in Example 1 in which calibrations were performed by a calibration device in a non-destructive inspection/measurement system according to the first embodiment.

FIG. 7 A vector diagram illustrating the measurement results in Example 1.

FIG. 8 A graph illustrating the measurement results in Example 2 in which calibrations were performed by a calibration device in a non-destructive inspection/measurement system according to the first embodiment.

FIG. 9 A graph illustrating the measurement results in Example 3 in which calibrations were performed by a calibration device in a non-destructive inspection/measurement system according to the first embodiment.

FIG. 10 An overall vector diagram for cases of measurement at temperatures of 25° C. and 58° C. using sinusoidal signals of five mutually different frequencies.

FIG. 11 A vector diagram measured at 33 Hz in FIG. 10.

FIG. 12 A vector diagram measured at 39 Hz in FIG. 10.

FIG. 13 A vector diagram measured at 57 Hz in FIG. 10.

FIG. 14 A vector diagram measured at 69 Hz in FIG. 10.

FIG. 15 A vector diagram measured at 87 Hz in FIG. 10.

FIG. 16 A graph showing the results of measurement of a carbon steel pipe in Example 4 in which calibrations were performed by a calibration device in a non-destructive inspection/measurement system according to the first embodiment.

FIG. 17 A graph showing the results of measurement of a carbon steel pipe in a comparative example using a conventional technique.

FIG. 18 A graph comparing the temperature characteristics of the measurement results by the technique of Example 4 shown in FIG. 16 and the measurement results by the technique of the comparative example shown in FIG. 17.

FIG. 19 A diagram illustrating the structure of a test object in Example 5 in which calibrations were performed by a calibration device in a non-destructive inspection/measurement system according to the second embodiment.

FIG. 20 A graph showing the measurement results in a comparative example using a conventional technique.

FIG. 21 A graph showing the measurement results in the above-mentioned Example 5.

DETAILED DESCRIPTION OF THE INVENTION

Herebelow, by referring to the attached drawings, modes for carrying out the calibration device of the non-destructive inspection/measurement system and the non-destructive inspection/measurement method according to the present invention will be explained on the basis of the drawings.

First Embodiment

FIG. 1 is a diagram illustrating the structure of a non-destructive inspection/measurement system and calibration device according to a first embodiment of the present invention.

[Non-Destructive Inspection/Measurement System]

As illustrated in FIG. 1, the non-destructive inspection/measurement system 10 comprises a sensor 1 and a measurement device 3.

In this case, the test object 2 that is to be inspected comprises a tubular pipe body (test object body) 2a, a thermal insulation material 2b covering the outer circumferential portion of the pipe body 2a, and an outer covering material (adjacent body) 2c covering the outer circumference of the thermal insulation material 2b. In FIG. 1, only a portion of the test object 2, lying above the central axis in a section view, is shown.

The pipe body 2a is made of a metal such as, for example, carbon steel, that is both magnetic and conductive.

The thermal insulation material 2b is formed to a predetermined thickness from a material that is non-magnetic and non-conductive, such as calcium silicate, glass wool. Instead of providing this thermal insulation material 2b, it is possible to simply provide a space between the pipe body 2a and the outer covering material 2c.

The outer covering material 2c is formed from a metal material exhibiting at least one property of conductivity and magnetism such as aluminum, zinc-plated iron sheets (galvanized iron) or tin-plated iron sheets, stainless steel or the like.

The sensor 1 comprises a detector 11 and an exciter 12.

The sensor 1 comprises the detector 11 in a central portion and comprises the exciter 12 on the outer circumferential portion of the detector 11.

The detector 11 comprises a detection core 111 and a detection coil 112.

The detection core 111 comprises a magnetic body such as ferrite.

Additionally, the detection coil 112 is wound around the detection core 111.

The detector 11 formed in this way is arranged so that the detection coil 112 faces the test object 2 in a state wherein the central axis of the detection coil 112 is aligned with a line that is normal to the test object 2.

The exciter 12 comprises an excitation core 121 and an excitation coil 122.

The excitation core 121 comprises a magnetic body such as ferrite.

Additionally, the excitation coil 122 is wound around the excitation core 121.

In FIG. 1, the exciter 12 is arranged with the detector 11 at the center. Thus, the excitation coil 122 is disposed to the outside of the detection coil 112.

The excitation core 121 comprising the excitation coil 122 is arranged so that the central axis thereof is aligned with the central axis of the detector 11.

The measurement device 3 comprises a computer (detection processing unit) 301, a digital/analog converter (DAC) 302, a power amplifier 303, a multiplexer 304, an analog/digital converter (ADC) 305 and a display/data acquisition unit 306.

The computer 301 digitally generates a combined signal of sinusoidal signals having a single frequency or multiple frequencies. The digital to analog converter 302 converts the combined signal generated by the computer 301 to an analog signal. The power amplifier 303 amplifies the analog signal from the digital/analog converter 302 and supplies the amplified signal to the excitation coil 122 of the sensor 1. Due to this analog signal, the excitation coil 122 is excited by an alternating voltage. When the excitation coil 122 is excited, a change occurs in the magnetic field in the pipe body 2a. The output voltage of the detection coil 112 changes due to the electric current that flows in accordance with magnetic field changes in the pipe body 2a.

The multiplexer 304 takes, as inputs, the voltage generated in the detection coil 112 and the voltage applied to the excitation coil 122. The analog to digital converter 305 converts the output of the multiplexer 304 to a digital signal and outputs the digital signal to the computer 301. The computer 301 performs measurement and analysis processes using the output from the analog to digital converter 305. The display/data acquisition unit 306 displays and acquires the data resulting from the measurement and analysis processes in the computer 301.

When measuring the pipe body 2a using the non-destructive inspection/measurement system 10 as described above, while moving the sensor 1 along the outer surface of the test object 2, a sinusoidal signal or a combined signal comprising a plurality of sinusoids of different frequencies is generated by the computer 301 to excite the excitation coil 122 at calibration points where the thickness of the pipe body 2a is known. The computer 301 detects the amplitude ratios and the phase differences of the output voltage of the detection coil 112 in response to excitation by the excitation coil 122.

In this case, if measurements are to be made by changing the sinusoidal signal between multiple frequencies, the first measurement is performed by suing a sinusoid of frequency A, and the amplitude ratio and phase difference of the output voltage of the detection coil are measured and set as the measurement values at the frequency A. For the second measurement, the sinusoid is changed to one of the frequency B, which is different from the frequency A, and the amplitude ratio and phase difference at the frequency B are determined.

Additionally, if measurements are to be made by using a combined signal comprising a plurality of sinusoids of mutually different frequencies, the combined signal obtained by combining a sinusoid of the frequency A and a sinusoid of the frequency B beforehand will no longer be a sinusoid, but this combined signal is used to excite the excitation coil, and the amplitude ratio and phase difference of the output voltage of the detection coil are measured. At this time, the output of the detection coil will not be a sinusoidal signal. However, by using a Fast Fourier Transform (FFT) as described below, it is possible to detect the amplitude ratio and phase difference for each of the sinusoids of the frequency A and the frequency B simultaneously, so the measurement efficiency is high.

In general, the waveform of a sinusoidal signal can be uniquely identified by determining three constants, i.e., the frequency, the amplitude and the phase thereof. Therefore, in the computer 301, a Fast Fourier Transform (FFT) is used as a waveform analysis processing method for calculating the amplitude and the phase.

As the amplitude, the voltage value is normally taken, but the output of the detection coil 112 will often vary de to variable factors such as the temperature, voltage variations. Therefore, in order to suppress variations in the measurement system, an amplitude ratio which is the ratio between the output voltage of the detection coil 112 and the input voltage of the excitation coil 122, which is the denominator, is used, thus providing further generalization and allowing highly precise data acquisition.

As the phase, the phase difference between the input phase of the excitation coil 122 and the output phase of the detection coil 112 was indicated in radians.

In this case, in the computer 301, the frequency series of the frequencies of the generated sinusoidal signals was set to be a base-3 prime number series in order to prevent the so-called aliasing effect in which higher harmonics of the signals fall into the frequency ranges of other signals. For example, in the embodiment, 33, 39, 57, 69 and 87 Hz are used. The reason for avoiding the vicinity of 50 to 60 Hz in order to prevent the influence of power source noise.

[Calibration Device]

The calibration device 5 is connected to the measurement device 3 of the non-destructive inspection/measurement system 10. It is also possible to incorporate the calibration device 5 into the measurement device 3.

The calibration device 5 performs a calibration with respect to the thickness of a pipe body 2a as measured, by the non-destructive inspection/measurement system 10, at multiple calibration points of known thickness on the pipe body 2a, and sets up an estimating equation on the basis of the calibration.

The calibration device 5 receives, from the computer 301 in the measurement device 3, an output signal indicating the amplitude ratios and phase differences of voltage changes detected by the non-destructive inspection/measurement system 10. The calibration device 5 prepares an estimating equation for estimating the thickness of the test object 2 using these amplitude ratios and phase differences as variables. Furthermore, by solving multivariable simultaneous equations that are obtained by entering, into the estimating equations, the known thickness values and measured element values at a plurality of calibration points at which the thickness of the test object 2 is known, the coefficients and constants in the estimating equation are determined. In other words, a test object thickness estimating equation is established.

The calibration device 5 calculates the thicknesses at specific locations by using the estimating equation with the coefficients and constant determined by solving the multivariable simultaneous equations, and the amplitude ratios and phase differences of the voltage changes detected by the non-destructive inspection/measurement system 10.

In this case, the calibration device 5 may solve the simultaneous equations online to estimate the thicknesses. However, from the aspect of measurement speed, it is also possible to acquire data only for amplitude ratios and phase differences, and coordinate values indicating the measurement points thereof, online, and to solve the simultaneous equations offline, in order to estimate the thicknesses at those points.

As the method for solving the multivariable simultaneous equations, the inverse matrix method is commonly used. However, when performing the calculations in the calibration device 5, it is preferable to use the Cramer method, which is held to have little risk of losing significant digits.

The calibration device 5 performs the calibration by using a plurality of different calibration conditions at each calibration point, and entering the amplitudes and phase differences of the output voltage of the detection coil 112 into the simultaneous equations for each of the calibration conditions.

More specifically, the calibration device 5 preferably calibrates the estimating equation used for measuring the thickness of the pipe body 2a by entering the amplitudes and phase differences of the output voltage of the detection coil 112 as variables in the simultaneous equations for each of two or more mutually different temperature conditions.

Additionally, the calibration device 5 calibrates the estimating equation used for measuring the thickness of the pipe body 2a by entering the amplitudes and phase differences of the output voltage of the detection coil 112 as variables in the simultaneous equations for each of three or more locations with mutually different thicknesses.

Additionally, the calibration device 5 preferably performs calibrations by using a plurality of different frequencies for the sinusoidal signals or the multiple sinusoids constituting the combined signals applied to the excitation coil 122, and entering the amplitudes and phase differences of the output voltage of the detection coil 112 as variables in the simultaneous equations for each of the frequencies.

The calibration of the calibration device 5 can be performed simultaneously with the measurement operations in the non-destructive inspection/measurement system 10 so as to acquire and display the thickness estimate values in real-time. However, by focusing only on the acquisition of the raw data for the position information and the amplitude ratio and phase difference at each measurement point during the measurement operations in the non-destructive inspection/measurement system 10, and performing the calibration and thickness estimating in the calibration device 5 offline, it becomes possible to carry out trials using different calibration conditions, so a high level of conveniences is obtained.

According to the calibration device for a non-destructive inspection/measurement system and the non-destructive inspection/measurement method described above, it is possible to perform calibrations with high precision in accordance with various condition changes in the test object 2 by performing the calibrations using multiple different calibration conditions at each of a plurality of calibration points of known thickness on the pipe body 2a.

Additionally, by performing the calibrations under a plurality of different temperature conditions, the calibration device allows the measurement precision to be maintained at a high precision level, even it the temperature conditions vary while measuring the pipe body 2a.

When performing calibrations at two or more different temperatures, if it is possible to obtain measurement values at three temperatures, such as at 25° C., 30° C. and 55° C., then the precision can be further raised by using nine-variable simultaneously equations using four frequencies. In this case, if the mutually different first temperature and second temperature are close to each other, then it is possible, as a simplification method, to take the average values of the amplitude ratio and the phase difference detected when performing calibrations at the first temperature and the second temperature, and to use those values, together with the amplitude ratio and phase difference at the third temperature, in seven-variable simultaneous equations. However, higher precision can be obtained by using nine-variable simultaneous equations as mentioned above.

Additionally, by performing calibrations at three or more locations of mutually different thicknesses on the pipe body 2a, it is possible to maintain the measurement precision at a high precision level at each of the portions with different thicknesses when measuring the pipe body 2a.

Furthermore, by performing calibrations using a plurality of different frequencies for the sinusoidal signals or the multiple sinusoids constituting the combined signals applied to the excitation coil 122, it is possible to keep the measurement precision at a high precision level.

A measurement method in which calibrations are performed at multiple frequencies and the amplitude ratios and phase differences are entered into the calibration in such a manner is beneficial as it allows variable elements such as other environmental variations to be canceled or reduced. Additionally, there is no need to acquire or input the temperature value itself, and the affection of temperature can be compensated by entering the measurement values into the calibration when the test object 2 enters the steady state at the temperature, so the calibration can be performed very easily.

By performing the above-mentioned calibration process, the precision of the thickness estimate values can be raised over a wide range in a test object 2 having locations with different thicknesses.

Additionally, it is possible to eliminate or lessen the influence of temperature on the thickness estimate values of the test object 2.

The function of the calibration device 5 above-mentioned may be performed by the computer 301 separately.

Second Embodiment

Next, a second embodiment of the calibration device for a non-destructive inspection/measurement system and the non-destructive inspection/measurement method according to the present invention will be explained. In the second embodiment explained below, the features that are the same as those in the above-mentioned first embodiment will be indicated by the same reference symbols in the drawings, and their explanations will be omitted.

In the non-destructive inspection/measurement system 10 in the present embodiment, as with the non-destructive inspection/measurement system 10 in the above-described first embodiment, the non-destructive inspection/measurement system 10 comprises a sensor 1 and a measurement device 3. This non-destructive sensor measurement system 10 excites an excitation coil 122 with an alternating voltage, using a sinusoidal signal or a combined signal comprising a plurality of sinusoids having mutually different frequencies, generated by a computer 301, and measures (estimates) the thickness of a test object 2 by using the output voltage from the detection coil 112 and the input voltage to the excitation coil 122.

The calibration device 5 in the present embodiment is connected to the measurement device 3 in such a non-destructive inspection/measurement system 10.

The test object 2 comprises a plurality of components, including a pipe body 2a, and an outer covering material 2c having a thermal insulation material 2b provided between the outer covering material and the pipe body 2a.

When the test object 2 comprises two or more components in this manner, the calibration device 5 performs the calibrations by entering, in simultaneous equations, the measurement values for the amplitude ratio and phase difference in the pipe body 2a, which is the component having the locations that are being measured, including the influence of the outer covering material 2c, which is an adjacent body that affects the measurements thereof, and the measurement values for the amplitude and phase difference at different temperatures in those locations. In other words, the thickness of the pipe body 2a is calibrated by entering, as variables in simultaneous equations, the amplitudes and phase differences of the output voltage of the detection coil 112 for each of multiple different thicknesses of the pipe body 2a, and distances between the pipe body 2a and the outer covering material 2c that is provided so as to be spaced from the pipe body 2a.

By performing calibrations by using multiple different thicknesses of the pipe body 2a and distances between the test object 2 and the outer covering material 2c as described above, it is possible to maintain the measurement precision at a high precision level even if the thickness of the pipe body 2a or the distance between the test object 2 and the outer covering material 2c varies when measuring the pipe body 2a.

With the above-described second embodiment, it is possible to make highly precise measurements by reducing or eliminating the influence of the configuration of the test object or adjacent bodies that influence the measurement of locations on the test object that are to be measured, such as, in the case where the test object is formed from a plurality of metal bodies, the relative distances (layer spacing) therebetween and the orientations thereof, and in the case of adjacent bodies rather than portions of the test object, for example, caulked portions of the outer covering body of a pipe, or a flange portion, an elbow portion or the like of a pipe.

Additionally, for pipes or the like, highly precise measurements can be made by reducing or eliminating the influence of conductive fluids or magnetic fluids flowing inside the pipes.

EXAMPLES

Next, the calibration device for a non-destructive inspection/measurement system and the non-destructive inspection/measurement method indicated in the above-described embodiments were tested, so the results thereof will be explained.

As shown in FIG. 2, in the test object 2, a pipe body 2a comprising a magnetic and conductive carbon steel pipe SS400-65A having a material thickness of 4.2 mm and an outer diameter of 76.3 mm was used. The test object 2 was worked to respective thicknesses of 2.4 mm and 3.4 mm at the ends thereof, while leaving the thickness at 4.2 mm in the central part.

Additionally, a hemispherical artificial flaw K of 20 mmϕ and a depth of 2 mm was formed on the inner circumferential surface of the central part of the pipe body 2a in the test object 2.

In measuring the thickness of this test object 2 with the non-destructive inspection/measurement system 10, the frequency series of the frequencies of the sinusoidal signals or the combined signals comprising a plurality of sinusoidal signals of mutually different frequencies generated by the computer 301 was set to be a base-3 prime number series in order to prevent the so-called aliasing effect in which higher harmonies of the signals fall into the frequency ranges of other signals, and 33, 39, 57, 69 and 87 Hz were used. The reason for avoiding the vicinity of 50 to 60 Hz was in order to prevent the influence of power source noise.

Additionally, the sampling frequency was 24.576 Hz, and 8192 points were chosen as the number of sampling points with a view to achieving an adequately high precision.

FIGS. 3 and 4 indicate specific waveforms of the combined signals used for the measurements.

The combined signal S1 illustrated in FIG. 3 is a combination of two sinusoids of the two frequencies 33 Hz and 39 Hz having the same amplitude. This combined signal S1 was a burst signal having a preamble section (leading section) S11 of 2048 points in which the amplitude gradually rose, exponentially, from a signal-less interval to the steady state, a post-amble section (trailing section) S12 and 2048 points in which the amplitude gradually fell from the steady state to a signal-less interval, and a sampling point (measurement signal section) S13 of 8192 points, provided between the preamble section S11 and the post-amble section S12, which is in the steady state, for inputting data to a Fast Fourier Transform (FFT). Though not shown, there was no signal before or after the above-described S1.

The combined signal S2 shown in FIG. 4 was formed by combining sinusoids of the three frequencies 33 Hz, 39 Hz and 69 Hz. This combined signal S2 was also a burst signal having a preamble section S21, a post-amble section S22 and a sampling point (measurement signal section) S23 provided between the preamble section S21 and the post-amble section S22.

Thus, using of burst signal can eliminate the window function filter which is necessary for applying FFT to the continuous waves to avoid the aliasing.

Depending on the test object 2, there may be some locations that are strongly magnetic, so that when scanning for measurements, residual magnetism arises, resulting in measurement error in the case of repeated measurement. In such a case, it is possible to avoid measurement error due to the influence of residual magnetism by using, as the combined signals S1 and S2, burst signals that gradually rise from a signal-less interval, enter the steady state, then gradually fall from the steady state to a signal-less interval, as shown in FIGS. 3 and 4, instead of continuous signals. Additionally, using burst signals as the combined signals S1 and S2 also has the advantage of allowing the capabilities, including the operation speeds, of hardware resources such as the computer 301, the digital/analog converter 302, the multiplexer 304 and the analog/digital converter 305 to be maximized.

Additionally, for the temperature measurements, since electrical means such as thermocouples affect eddy currents and thus affect the measurement system, a classic alcohol rod-type thermometer was used. However, there was no need to acquire and input the numerical values for the temperature themselves, and the thermometer was used only to determine whether or not the temperature had reached the steady state.

Comparative Examples

For the purpose of comparison, a non-destructive inspection/measurement system 10 similar to that described above was used to measure a test object after calibration at only two points on the test object using a single frequency.

In this comparative example, the amplitude ratios and phase differences at the single frequency were detected, and the amplitude ratios and phase differences obtained at the respective calibration points were entered into three-variable simultaneous equations as in Equation (1) to determine constants and coefficients for the variables, and to thereby determine an equation for estimating the thickness of the test object. Then, the determined estimating equation was used to actually measure the thickness of the test object. Table 1 shows the simultaneous equations in table form for each calibration point, and the coefficients and constants obtained by solving the equations. The variable A in the equations indicates the amplitude ratio, and the variable P indicates the phase difference.

[Equation 1]

$$\begin{cases} aA_1 + bP_1 + c = t_1 \\ aA_2 + bP_2 + c = t_2 \\ aA_3 + bP_3 + c = t_3 \end{cases} \quad (1)$$

TABLE 1

Single Frequency Measurement, 33 Hz, Lift Off (LO)

| Coefficients of Variables in Simultaneous Equations | | a | b | c |
| --- | --- | --- | --- | --- |
| Determined Coefficient Values | | −8.018237 | 107.56992 | 15.37572 |
| Temperature (° C.) | Calibration Point | Amplitude Ratio | Phase Difference (rad) | t (mm) |
| 25 | A1, LO | 2.22894714 | 0.0554272 | 3.4 |
| 25 | B1 | 2.17743921 | 0.0509762 | 3.4 |
| 25 | C1 | 1.99395366 | 0.028003 | 2.4 |

As shown in Table 1, the calibration points, measured at room temperature (25° C.), were two calibration points at which the thickness of the test object was different, i.e., point B1 at which the thickness was 3.4 mm and point C1 at which the thickness was 2.4 mm. Additionally, the measurement values at three points were entered into the simultaneous equations of Equation (1), these being the measurement values for the amplitude ratios and phase differences of the voltage changes detected by the detection coil 112 in the sensor 1 at the points B1 and C1, and the measurement values for the amplitude ratio and the phase difference when the lift off (abbreviated to LO in the table), which is the distance between the upper surface of the test object 2 and the lower surface of the sensor 1, was changed from 3 mm to 3.2 mm at the point A1 having a thickness of 3.4 mm.

As shown in FIG. 5, at room temperature (25° C.), the thickness were accurately measured at the two points on the test object that were entered as calibration values, i.e., point B1 at which the thickness was 3.4 mm and point C1 at which the thickness was 2.4 mm, and also for the thickness of 3.4 mm even when changing the lift off. However, at a point having the thickness of 4.2 mm, which was not entered as a calibration value, the thickness measurement value was 4.6 mm, so the value largely deviated from the expected value of 4.2 mm.

Further thickness measurements were made when feeding hot air inside the test object 2 by a hot air blower to raise the temperature of the space inside the pipe body 2a to 58° C., during the process of temperature increase and in the final steady state.

The measurement results thereof are shown in FIG. 5. In FIG. 5, the horizontal axis represents the time axis, so continuous measurements were made during the temperature increase process. As a result thereof, at 58° C., the thickness was measured to be 2.93 mm at a location having an actual thickness of 3.4 mm, the thickness was measured to be 2.15 mm at a location having an actual thickness of 2.4 mm, and the thickness was measured to be 4.05 mm at a location having an actual thickness of 4.2 mm.

Thus, as the temperature of the test object 2 changes, the thickness measurement precision falls significantly. In other words, the temperature coefficient is large.

Example 1

In the present Example 1, an equation for estimating the thickness of a test object was determined, in a calibration device 5 in a non-destructive inspection/measurement system 10 similar to that described above, by determining the constants and coefficients of variables by entering, in the three-variable simultaneous equations in Equation (1), amplitude ratios and phase differences obtained at three calibration points having mutually different thicknesses on a test object, using a single frequency. Additionally, the determined estimating equation was used to actually measure the thickness of a test object. Table 2 shows the simultaneous equations in table form for each calibration point, and the coefficients and constant obtained by solving the equations.

With the frequency of the sinusoidal signal set to 33 Hz and a room temperature (25° C.), three points, i.e. point B1 at which the thickness was 3.4 mm, point C1 at which the thickness was 2.4 mm and point D1 at which the thickness was 4.2 mm, were used as the calibration points. At each calibration point, the measurement values for the amplitude ratios and phase differences of the voltage changes detected by the detection coil 112 when excited with the excitation coil 122 were entered into the three-variable simultaneous equations of Equation 1.

TABLE 2

Single Frequency Measurement, 33 Hz

| Coefficients of Variables in Simultaneous Equations | | a | b | c |
|---|---|---|---|---|
| Determined Coefficient Values | | −8.018237 | 107.56992 | 15.37572 |
| Temperature (° C.) | Calibration Point | Amplitude Ratio | Phase Difference (rad) | t (mm) |
| 25 | D1 | 2.1018297 | 0.0527773 | 4.2 |
| 25 | B1 | 2.17743921 | 0.0509762 | 3.4 |
| 25 | C1 | 1.99395366 | 0.028003 | 2.4 |

After calibrating the system in this way, the thickness of the test object was measured.

The results are shown in FIG. 6. As shown in FIG. 6, there were slight deviations when the lift off (LO) was changed, but all three points, i.e., point C1 at which the thickness was 2.4 mm, point B1 at which the thickness was 3.4 mm and point D1 at which the thickness was 4.2 mm, were measured precisely in a 25° C. environment. In particular, the measurement at point D1, at which the thickness was 4.2 mm, was greatly improved in comparison to FIG. 5, which shows a comparative example. Therefore, in the present example, it was possible to handle test objects having little temperature variation, at least near room temperature.

However, in the present example, when the temperature was raised to 58° C., error arose with respect to the expected values (the actual thicknesses) at all of points B1, C1 and D1, so variations occurred due to temperature.

FIG. 7 is a vector diagram illustrating Example 1, with the amplitude ratio on the horizontal axis and the phase difference on the vertical axis. The subscript 1 in B1, C1, D1 and the like indicates a value at room temperature (25° C.) and the subscript 2 indicates a value at 58° C. As is clear from FIG. 7, the coordinates for the amplitude ratio and the phase difference at point D1 do not lie on the straight line connecting the coordinates of the point B1 and the point C1, making it clear that it is insufficient to use just the points B1 and C1 as calibration points to be entered into the simultaneous equations, and that point D1 must also be entered.

This is because the thicknesses are not distributed on the one-dimensional straight line B1-C1, but rather are distributed on the B1-C1-D1 plane, i.e., a two-dimensional amplitude ratio-phase difference plane, and a minimum of three points are necessary to define that plane. The detection precision is clearly higher in the vicinity of these three points, including interpolations and extrapolations thereof. Therefore, high-precision measurements across a wide range can be made by expanding to four or five points.

In FIG. 7, the single-dotted chain lines indicate so-called contour lines that are drawn using the constants and coefficients for a, b and c in Table 2, as determined by solving the three-variable simultaneous equations in Equation (1). At room temperature (25° C.), the points A1, B1 and C1, at which the thicknesses are 2.4 mm, 3.4 mm and 4.4 mm, are distributed on the contour line F1 in the amplitude ratio-phase difference plane. The points A2, B2 and C2, at the temperature 58° C., lie on a contour line F2 that is shifted from the points A1, B1 and C1, so the influence of temperature is strong.

Example 2

In the present Example 2, an equation for estimating the thickness of a test object was determined, in a calibration device 5 in a non-destructive inspection/measurement system 10 similar to that described above, by performing a calibration by entering in simultaneous equations, measurement values of the amplitudes and phase differences in the test object 2 at mutually different temperatures, using a combined signal of sinusoids of multiple frequencies. Then, the determined estimating equation was used to actually measure the thickness of the test object.

In Example 2, two frequencies, i.e., 33 Hz and 57 Hz, were used as the frequencies for the sinusoids in the combined signal applied to the excitation coil 122, in order to increase the variables in the simultaneous equations. Additionally, at 25° C., three points, i.e., point B1 at which the thickness was 3.4 mm, point C1 at which the thickness was 2.4 mm and point D1 at which the thickness was 4.2 mm, were used as the calibration points, and the 58° C., two points, i.e., point B2 at which the thickness was 3.4 mm and point C2 at which the thickness was 2.4 mm, were used as the calibration points. These five points B1, B2, C1, C2 and D1 were entered for the calibration, and the five-variable simultaneous equations shown in Equation (2) were used. Table 3 shows the simultaneous equations in table form for each calibration point, and the coefficients and constants obtained by solving the equations.

[Equation 2]

$$\begin{cases} aA_{11} + bP_{11} + cA_{21} + dP_{21} + e = t_1 \\ aA_{12} + bP_{12} + cA_{22} + dP_{22} + e = t_2 \\ aA_{13} + bP_{13} + cA_{23} + dP_{23} + e = t_3 \\ aA_{14} + bP_{14} + cA_{24} + dP_{24} + e = t_4 \\ aA_{15} + bP_{15} + cA_{25} + dP_{25} + e = t_5 \end{cases} \quad (2)$$

TABLE 3

When Using Two Frequencies (33, 57 Hz)

| Coefficients of Variables in Simultaneous Equations | | a | b | c | d | e |
|---|---|---|---|---|---|---|
| Determined Coefficient Values | | −691.944331 | 1292.843961 | 712.99741 | −406.204875 | −44.4181704 |
| Frequency (Hz) | | 33 | | 57 | | |
| Temperature (° C.) | Calibration Point | Amplitude Ratio | Phase Difference (rad) | Amplitude Ratio | Phase Difference (rad) | t (mm) |
| 25 | D1 | 2.101829703 | 0.052777311 | 2.05091653 | 0.067856605 | 4.2 |
| 25 | B1 | 2.177439211 | 0.050976203 | 2.127624748 | 0.069940869 | 3.4 |
| 58 | B2 | 2.185182219 | 0.048231793 | 2.138398989 | 0.066928058 | 3.4 |
| 25 | C1 | 1.993968984 | 0.028003858 | 1.973620637 | 0.041499542 | 2.4 |
| 58 | C2 | 1.993165377 | 0.026179353 | 1.974726101 | 0.039001898 | 2.4 |

When the thickness of the test object was measured by means of an estimating equation obtained by solving the above-described simultaneous equations, precise measurements were made at 25° C. for all three points, i.e., point C1 at which the thickness was 2.4 mm, point B1 at which the thickness was 3.4 mm and point D1 at which the thickness was 4.2 mm, as shown in FIG. 8. Additionally, it was verified that highly precise measurements were possible for point B2 at which the thickness was 3.4 mm and at point C2 at which the thickness was 2.4 mm, which were entered for calibration, so that the temperature compensation was achieved.

However, as the point D1 at which the thickness was 4.2 mm, precise measurements were made at 25° C., but a large deviation was exhibited at 58° C.

Example 3

In the present Example 3, an equation for estimating the thickness of a test object was determined, in a calibration device 5 in a non-destructive inspection/measurement system 10 similar to that described above, by performing a calibration by entering as calibration values in simultaneous equations, measurement values of the amplitudes and phase differences at three or more calibration points having different thicknesses on a test object 2, and by entering, in simultaneous equations, measurement values of the amplitudes and phase differences in the test object 2 at mutually different temperatures, using sinusoidal signals of multiple frequencies. Then, the determined estimating equation was used to actually measure the thickness of the test object.

In Example 3, three frequencies, i.e., 33 Hz, 39 Hz and 69 Hz, were used as the frequencies for the sinusoids in the combined signal applied to the excitation coil 122. For each frequency, at 25° C., three points, i.e., point B1 at which the thickness was 3.4 mm, point C1 at which the thickness was 2.4 mm and point D1 at which the thickness was 4.2 mm, were used as the calibration points, and at 58° C., three points, i.e., point B2 at which the thickness was 3.4 mm, point C2 at which the thickness was 2.4 mm and point D2 at which the thickness was 4.2 mm, were used as the calibrations points. These six points B1, B2, C1, C2, D1 and D2, and one further point with measurement values for the amplitude ratio and phase difference when the lift off was changed from 3 mm to 3.2 mm at 25° C., i.e., a total of seven points, were entered as the calibration points in the simultaneous equations in Equation (3).

Table 4 shows the simultaneous equations in table form for each calibration point, and the coefficients and constants obtained by solving the equations.

[Equation 3]

$$\begin{cases} aA_{11} + bP_{11} + cA_{21} + dP_{21} + eA_{31} + fP_{31} + g = t_1 \\ aA_{12} + bP_{12} + cA_{22} + dP_{22} + eA_{32} + fP_{32} + g = t_2 \\ aA_{13} + bP_{13} + cA_{23} + dP_{23} + eA_{33} + fP_{33} + g = t_3 \\ aA_{14} + bP_{14} + cA_{24} + dP_{24} + eA_{34} + fP_{34} + g = t_4 \\ aA_{15} + bP_{15} + cA_{25} + dP_{25} + eA_{35} + fP_{35} + g = t_5 \\ aA_{16} + bP_{16} + cA_{26} + dP_{26} + eA_{36} + fP_{36} + g = t_6 \\ aA_{17} + bP_{17} + cA_{27} + dP_{27} + eA_{37} + fP_{37} + g = t_7 \end{cases} \quad (3)$$

TABLE 4

When using Three Frequencies (33, 39, 69 Hz)

| Coefficients of Variables in Simultaneous Equations | | a | b | c | d | e | f | g |
|---|---|---|---|---|---|---|---|---|
| Determined Coefficient Values | | −183.488338 | 1494.21461 | 360.28892 | −1600.6351 | −176.69054 | 89.102216 | 4.183635 |
| Frequency (Hz) | | 33 | | 39 | | 69 | | |
| Temp. (° C.) | Calibration Point | Amplitude Ratio | Phase Difference (rad) | Amplitude Ratio | Phase Difference (rad) | Amplitude Ratio | Phase Difference (rad) | t (mm) |
| 25 | A1, L0 | 2.228947145 | 0.05542724 | 2.21516246 | 0.06255665 | 2.15060323 | 0.08310789 | 3.4 |
| 25 | B1 | 2.177439211 | 0.0509762 | 2.16506376 | 0.05753306 | 2.10654524 | 0.07664511 | 3.4 |
| 58 | B2 | 2.185182219 | 0.04823179 | 2.17366587 | 0.05457808 | 2.11808651 | 0.07363327 | 3.4 |
| 25 | C1 | 1.993968984 | 0.02800386 | 1.9887044 | 0.03229733 | 1.96281341 | 0.04760017 | 2.4 |

TABLE 4-continued

When using Three Frequencies (33, 39, 69 Hz)

| | Coefficients of Variables in Simultaneous Equations | a | b | c | d | e | f | g |
|---|---|---|---|---|---|---|---|---|
| 58 | C2 | 1.993165377 | 0.02617935 | 1.98832664 | 0.03023659 | 1.96477223 | 0.04493433 | 2.4 |
| 25 | D1 | 2.101829703 | 0.05277731 | 2.08846069 | 0.05824448 | 2.03115039 | 0.07273613 | 4.2 |
| 58 | D2 | 2.108492048 | 0.04970104 | 2.09602309 | 0.0550299 | 2.04116791 | 0.069583 | 4.2 |

The Thickness of the test object was measured by an estimating equation obtained by solving the above-described simultaneous equations. The results are shown in FIG. 9.

As shown in FIG. 9, for both temperatures 25° C. and 58° C., the thicknesses were measured with high precision at the point B1, B2 at which the thickness was 3.4 mm, at the point C1, C2 at which the thickness was 2.4 mm and at the point D1, D2 at which the thickness was 4.2 mm. In other words, the thickness of the test object was measured with high precision, regardless of temperature changes.

A vector diagram showing the results of measurement of the amplitude ratio and the phase difference at each of the frequencies, 33 Hz, 39 Hz, 57 Hz, 69 Hz and 87 Hz, of the sinusoids in the combined signal, are shown in FIG. 10. FIG. 11 to FIG. 15 show the results of FIG. 10 separately for each frequency. FIG. 11 is a diagram showing a vector diagram of the measurement results for the amplitude ratio and the phase difference at the frequency 33 Hz. FIG. 12 is a diagram showing a vector diagram of the measurement results for the amplitude ratio and the phase difference at the frequency 39 Hz. FIG. 13 is a diagram showing a vector diagram of the measurement results for the amplitude ratio and the phase difference at the frequency 57 Hz. FIG. 14 is a diagram showing a vector diagram of the measurement results for the amplitude ratio and the phase difference at the frequency 69 Hz. FIG. 15 is a diagram showing a vector diagram of the measurement results for the amplitude ratio and the phase difference at the frequency 87 Hz.

Example 4

In the present Example 4, an equation for estimating the thickness of a test object was determined, in a calibration device 5 in a non-destructive inspection/measurement system 10 similar to that described above, by performing a calibration by entering, as calibration values in simultaneous equations, measurement values of the amplitudes and phase differences at three or more calibration points having different thicknesses on the test object 2, and by entering, in simultaneous equations, measurement values of the amplitudes and phase differences in the test object 2 at mutually different temperatures, using a combined signal comprising multiple sinusoids of mutually different frequencies. Furthermore, the measurement position was shifted for each temperature at one calibration point.

In Example 4, three frequencies, i.e., 33 Hz, 39 Hz and 69 Hz, were used. For each frequency, at 25° C., three points, i.e., point B1 at which the thickness was 3.4 mm, point C1 at which the thickness was 2.4 mm and point D1 at which the thickness was 4.2 mm, were used as the calibration points, and at 55° C., three points, i.e., point B3 at which the thickness was 3.4 mm, point C3 at which the thickness was 2.4 mm and point D3 at which the thickness was 4.2 mm, were used as the calibration points. For each of the points B3, C3 and D2 at the temperature 55° C., the coordinates of the measurement locations were shifted by 5 mm in the X axis direction, along the central axis of the test object 2, with respect to the points B1, C1 and D1 at 25° C.

The measurement values of the amplitude ratio and the phase difference of output voltage of the detection coil 112 at each of the six points B1, B3, C1, C3, D1 and D3, and one point at which the lift off was changed from 3 mm to 3.2 mm at 25° C., i.e., a total of seven points, were entered as the calibration points in the simultaneous equations in Equation (3).

Table 5 shows the simultaneous equations in table form for each calibration point, and the coefficients and constants obtained by solving the equation.

TABLE 5

| | Coefficients of Variables in Simultaneous Equations | a | b | c | d | e | f | g |
|---|---|---|---|---|---|---|---|---|
| | Determined Coefficient Values | −250.705 | 1162.2201 | 405.275 | −1181.449 | −153.774 | 20.2632981 | 2.976512 |
| | Frequency (Hz) | 33 | | 39 | | 69 | | |
| Temp. (° C.) | Position X (mm) | Amplitude Ratio | Phase Difference (rad) | Amplitude Ratio | Phase Difference (rad) | Amplitude Ratio | Phase Difference (rad) | t (mm) |
| 25 | A1 LO 130 LO | 2.293707 | 0.0601062 | 2.278243 | 0.0678635 | 2.206752 | 0.08956861 | 3.4 |
| 25 | B1 130 | 2.239516 | 0.0555668 | 2.225549 | 0.0627354 | 2.160465 | 0.08310346 | 3.4 |
| 55 | B3 135 | 2.23443 | 0.0519879 | 2.22174 | 0.0588683 | 2.160881 | 0.07930462 | 3.4 |
| 25 | D1 325 | 2.140693 | 0.05535 | 2.126267 | 0.0609966 | 2.065428 | 0.07541289 | 4.2 |
| 55 | D3 330 | 2.140761 | 0.0514722 | 2.127521 | 0.0569475 | 2.069886 | 0.07135062 | 4.2 |
| 25 | C1 525 | 2.066999 | 0.0321252 | 2.060708 | 0.0370599 | 2.030086 | 0.05428786 | 2.4 |
| 55 | C3 530 | 2.066071 | 0.029939 | 2.060368 | 0.0345958 | 2.032691 | 0.05108987 | 2.4 |

The thickness of the test object was actually measured by using an estimating equation determined in this manner. During the measurements, the measurements were made by scanning a sensor 1 in the central axis direction (X axis direction) of the test object 2 at each of the temperatures 25° C. and 55° C.

The results are shown in FIG. 16.

As shown in FIG. 16, the measurement results for the thickness of the test object 2 at 25° C. and at 55° C. matched so well that no difference could be discerned therebetween. As a result, it was clear that, in the present Example 4, the temperature was able to be completely compensated. Additionally, a hemispherical artificial flaw K formed in the central portion of the test object 2 was also clearly detected.

Additionally, the physical positions of the calibration points at 25° C. and 55° C. did not need to be completely the same, nor was there a need for the temperatures to be completely the same at each calibration point.

Comparison Between Example 4 and Comparative Example

In order to compare present Example 4 with the comparative example based on a conventional method, measurements were made by scanning a sensor 1 in the central axis direction (X direction) of the test object 2, as with the above-described Example 4, at each temperature 25° C. and 55° C., using the method of the comparative example.

The results thereof are shown in FIG. 17 and Table 6.

TABLE 6

| Coefficients of Variables in Simultaneous Equations | a | b | c |
|---|---|---|---|
| Determined Coefficient Values | −9.31765 | 111.23198 | 18.08622 |
| Frequency (Hz) | | 33 | |

| Temperature (° C.) | Position | X (mm) | Amplitude Ratio | Phase Difference (rad) | t (mm) |
|---|---|---|---|---|---|
| 25 | A1 LO | 130 LO | 2.293707 | 0.0601062 | 3.4 |
| 25 | B1 | 130 | 2.239516 | 0.0555668 | 3.4 |
| 25 | C1 | 525 | 2.066999 | 0.0321252 | 2.4 |

As shown in FIG. 17, when comparing the state at 25° C. with the state at 55° C., the overall thickness of the test object is measured as being smaller at 55° C. than at 25° C. In other words, the temperature coefficient is large in the comparative example.

FIG. 18 is a graph comparing the measurement results in Example 4 with the measurement results in the comparative example. Additionally, Table 7 shows calculations of average values and standard deviations for the measurement results in Example 4 and the measurement results in the comparative example.

TABLE 7

| Δt = t_55° C. − t_25° C. (N = 160) | | |
|---|---|---|
| | With Temperature Compensation Calibration | Conventional Art |
| Average Value (mm) | 0.0258 | −0.317 |
| Standard Deviation (mm) | 0.0550 | 0.107 |

As shown in FIG. 18 and Table 7, the measurements in Example 4 indicated that the accurate temperature compensated measurements are possible.

Example 5

Next, tests were performed for the case in which the test object comprises a plurality of components. In other words, as shown in FIG. 1, when the test object 2 comprises a pipe body 2a, a thermal insulation material 2b and an outer covering material 2c, the test object 2 has a two-layer structure comprising two components, i.e. the pipe body 2a and the outer covering material 2c. In the case of such a structure, the distance between the outer covering material 2c and the pipe body 2a, i.e., the interlayer spacing, is not necessarily uniform, and in some cases, it may change considerably depending on the location. Therefore, in Example 5, thickness measurements of such a pipe body 2a were made from outside the outer covering material 2c.

In this Example 5, as shown in FIG. 19, a first-layer component 201 (corresponding to the outer covering material 2c) and a second-layer component 202 (corresponding to the pipe body 2a) were provided, with a spacing therebetween (corresponding to the thermal insulation material 2b), as the test object 2 for Example 5. As the first-layer component 201, a flat aluminum sheet having a sheet thickness of t1=1 mm was used. A flat aluminum sheet was also used for the second-layer component 202, and measurements were made for the case in which the thickness t2=3 mm and the case in which the thickness t2=4 mm. When setting the thickness of the second-layer component 202 to 4 mm, a flat sheet having a thickness of 1 mm was brought into tight contact with a flat sheet having a thickness of 3 mm, thus obtaining the equivalent of a thickness of 4 mm. This was done in order to make the thermal response of the second-layer component 202 faster and to simulate actual thinning.

Additionally, aluminum was used for the material of the test object 2 rather than carbon steel or stainless steel because it has good thermal conductivity, a lower specific resistance, and a high temperature coefficient, so the influence of temperature changes will appear more prominently.

Additionally, the interlayer spacing S between the first-layer component 201 and the second-layer component 202 was set to both S=45 mm and to S=26.2 mm in order to verify the influence of changes in the interlayer spacing.

Calibrations were performed by entering, in three-variable simultaneous equations, the amplitude ratios and phase differences of power changes output from the detection coil 112, by the above-described method of the comparative example, using only a single frequency, 33 Hz, as the frequency of the sinusoidal signal applied to the excitation coil 122, at a temperature of 25° C. and an interlayer spacing, between the two layers, of 45 mm. Table 8 shows the constants and the coefficients in the simultaneous equations for this case.

TABLE 8

| Coefficients of Variables in Simultaneous Equations | | | a | b | c |
|---|---|---|---|---|---|
| Determined Coefficient Values | | | 4.332832 | 18.24071 | −47.8191 |
| Temperature (° C.) | Interlayer Spacing (mm) | t2 (mm) | A 33 Hz | P 33 Hz | t2 (mm) |
| 25 | 45 | 4 | 2.984788 | 2.131855 | 4 |
| 25 | 45 | 3 | 3.044369 | 2.06288 | 3 |
| 25 | 45 | 4 | 2.985038 | 2.131795 | 4 |

FIG. 20 shows the measurement results of a test object when calibrations were performed by the method of the comparative example. The measurements were made by changing the temperature between 25° C. and 55° C., and at each temperature, changing the interlayer spacing between 45 mm and 46.2 mm. At this time, thickness measurements were made for the case in which the thickness of the second-layer component 202 was 3 mm, and for the case in which the thickness was 4 mm.

As shown in FIG. 20, when the temperature was changed between 25° C. and 55° C., and at each temperature, the interlayer spacing was changed between 45 mm and 46.2 mm, error arose in the measurement values relative to the actual thicknesses (2 mm, 4 mm), which were the expected values, for both thicknesses, 3 mm and 4 mm, of the second-layer component 202. In particular, the error was large when the temperature was 55° C.

As opposed thereto, in the present Example 5, calibrations were performed at four frequencies, i.e., 33 Hz, 39 Hz, 57 Hz and 69 Hz, for all combinations of interlayer spacings of 45 mm and 46.2 mm, temperatures of 25° C. and 55° C., and thickness of 3 mm and 4 mm for the second-layer component 202. Table 9 shows the constants and coefficients in the simultaneous equations when calibrations were performed by entering the amplitude ratios and phase differences in nine-variable simultaneous equations in this manner.

TABLE 9

| Coefficients of Variables in Simultaneous Equations | | | a | b | c | d | e | f | g | h | i |
|---|---|---|---|---|---|---|---|---|---|---|---|
| Determined Coefficient Values | | | −38.793 | 68.29421 | 25.5939 | −30.741 | −46.5842 | −152.935 | 72.62763 | 66.86321 | 129.8439 |
| Temp. (° C.) | Inter-layer spacing (mm) | t2 (mm) | A 33 Hz | P 33 Hz | A 39 Hz | P 39 Hz | A 57 Hz | P 57 Hz | A 69 Hz | P 69 Hz | t2 (mm) |
| 25 | 45 | 4 | 2.984788 | 2.131855 | 2.713813 | 2.238019 | 2.288262 | 2.477687 | 2.148237 | 2.590254 | 4 |
| 25 | 45 | 3 | 3.044369 | 2.06288 | 2.73839 | 2.174016 | 2.265778 | 2.430775 | 2.114782 | 2.554858 | 3 |
| 25 | 46.2 | 3 | 3.023612 | 2.069596 | 2.722018 | 2.180876 | 2.256208 | 2.437726 | 2.108351 | 2.561594 | 3 |
| 25 | 46.2 | 4 | 2.961396 | 2.140131 | 2.694347 | 2.2467 | 2.277896 | 2.485751 | 2.141462 | 2.598255 | 4 |
| 55 | 45 | 3 | 3.180519 | 2.020501 | 2.847307 | 2.132082 | 2.330194 | 2.390485 | 2.162677 | 2.516867 | 3 |
| 55 | 46.2 | 3 | 3.167501 | 2.023605 | 2.837074 | 2.135773 | 2.321207 | 2.39305 | 2.155393 | 2.519276 | 3 |
| 55 | 46.2 | 4 | 3.072945 | 2.100101 | 2.781876 | 2.206456 | 2.327416 | 2.447657 | 2.175565 | 2.56218 | 4 |
| 55 | 45 | 4 | 3.049225 | 2.10527 | 2.764356 | 2.211471 | 2.314817 | 2.455128 | 2.167305 | 2.569433 | 4 |
| 25 | 45 | 4 | 2.985038 | 2.131795 | 2.713921 | 2.238105 | 2.28816 | 2.477583 | 2.148162 | 2.590231 | 4 |

FIG. 21 is a diagram showing the measurement results of a test object when calibrations were performed using the method of Example 5.

As shown in FIG. 21, the thickness of the component 202 was able to be precisely measured in each case when the temperature was changed between 25° C. and 55° C., and at each temperature, the interlayer spacing was changed between 45 mm and 46.2 mm, and the thickness of the second-layer component 202 was set to 3 mm and 4 mm. Thus, in Example 5, precise measurements were able to be made without being affected by changes in the interlayer spacing of the test object 2 or being affected by temperature changes.

Additionally, the measurement precision for the thickness of the test object was high even during the process of temperature change, and in this case, it is clear that the precision will be further increased by allowing the steady state to be reached at an intermediate temperature. In this way, it is possible to reduce or eliminate the influence of the structure of a test object or an adjacent body that affects the measurement of a location on a test object that is to be measured, and the influence of temperature, by incorporating the influences thereof into the calibrations.

INDUSTRIAL APPLICABILITY

According to the present invention, it is possible to precisely measure the thickness of test objects over a wide range of thicknesses and to compensate for temperature changes, so a non-contact electromagnetic induction measurement device having good temperature characteristics can be obtained. Thus, the present invention has high industrial utility and is highly convenient.

DESCRIPTION OF REFERENCE SYMBOLS 1 sensor
2 test object
2a pipe body (test object body)
2b thermal insulation material
2c outer covering material (adjacent body)
3 measurement device
5 calibration device (calibration processing unit)
10 non-destructive inspection/measurement system
11 detector
12 exciter
111 detection core
112 detection coil
121 excitation core
122 excitation coil
301 computer (detection processing unit)
302 analog converter
303 power amplifier
304 multiplexer
305 digital converter
306 data acquisition unit
K artificial flaw
S1, S2 combined signal
S11, S12 preamble section (leading section)
S12, S22 post-amble section (trailing section)
S13, S23 sampling point (measurement signal section)

The invention claimed is:
1. A calibration device for a non-destructive inspection/measurement system comprising an excitation coil and a detection coil, the excitation coil faces a test object body and excites the test object body, the detection coil faces the test object body and outputs a voltage in accordance with a magnetic field change generated in the test object body when the test object body is excited by the excitation coil, and a detection processing unit that applies, to the excitation coil for exciting the test object body, a sinusoidal signal or a combined signal comprising a plurality of sinusoids of mutually different frequencies, and that detects changes in the output voltage of the detection coil, the calibration device comprising:

a calibration processing unit that calibrates detection results in the detection processing unit by entering, as variables in simultaneous equations, amplitudes and phase differences of the output voltage of the detection coil at a plurality of calibration points of known thickness on the test object body, wherein the calibration processing unit performs calibrations by using multiple different calibration conditions at each of the calibration points, and entering, into the simultaneous equations, the amplitudes and phase differences of the output voltage of the detection coil for each of the calibration conditions.

2. The calibration device for a non-destructive inspection/measurement system according to claim 1, wherein the calibration processing unit calibrates detection results in the detection processing unit by entering, as variables in simultaneous equations, the amplitudes and phase differences of the output voltage of the detection coil for each of two or more mutually different temperature conditions.

3. The calibration device for a non-destructive inspection/measurement system according to claim 2, wherein the calibration processing unit calibrates detection results in the detection processing unit by entering, as variables in simultaneous equations, the amplitudes and phase differences of the output voltage of the detection coil for respective cases in which at least one of a spacing between the test object body and an adjacent body provided so as to be spaced with respect to the test object body and a thickness of the test object body is changed between multiple values.

4. The calibration device for a non-destructive inspection/measurement system according to claim 2, wherein the calibration processing unit calibrates detection results in the detection processing unit by entering, as variables in simultaneous equations, the amplitudes and phase differences of the output voltage of the detection coil for each of three or more locations, having mutually different thicknesses, on the test object body.

5. The calibration device for a non-destructive inspection/measurement system according to claim 2, wherein the calibration processing unit uses multiple different frequencies for the sinusoidal signals applied to the excitation coil, and calibrates detection results in the detection processing unit by entering, as variables in simultaneous equations, the amplitudes and phase differences of the output voltage of the detection coil at each frequency.

6. The calibration device for a non-destructive inspection/measurement system according to claim 2, wherein the calibration processing unit applies a combined signal comprising multiple sinusoids of mutually different frequencies to the excitation coil, and calibrates detection results in the detection processing unit by entering, as variables in simultaneous equations, the amplitudes and phase differences of the output voltage of the detection coil at each frequency.

7. The calibration device for a non-destructive inspection/measurement system according to claim 2, wherein the calibration processing unit applies to the excitation coil, as the sinusoidal signal or the combined signal, a burst signal having a leading section in which the amplitude gradually rises, a trailing section in which the amplitude gradually falls, and a measurement signal section, provided between the leading section and the trailing section, that is in the steady state and that is for data acquisition.

8. The calibration device for a non-destructive inspection/measurement system according to claim 2, wherein the calibration processing unit uses multi-variable simultaneous equations having five or more variables as the simultaneous equations.

9. The calibration device for a non-destructive inspection/measurement system according to claim 1, wherein the calibration processing unit calibrates detection results in the detection processing unit by entering, as variables in simultaneous equations, the amplitudes and phase differences of the output voltage of the detection coil for respective cases in which at least one of a spacing between the test object body and an adjacent body provided so as to be spaced with respect to the test object body and a thickness of the test object body is changed between multiple values.

10. The calibration device for a non-destructive inspection/measurement system according to claim 9, wherein the calibration processing unit calibrates detection results in the detection processing unit by entering, as variables in simultaneous equations, the amplitudes and phase differences of the output voltage of the detection coil for each of three or more locations, having mutually different thicknesses, on the test object body.

11. The calibration device for a non-destructive inspection/measurement system according to claim 9, wherein the calibration processing unit uses multiple different frequencies for the sinusoidal signals applied to the excitation coil, and calibrates detection results in the detection processing unit by entering, as variables in simultaneous equations, the amplitudes and phase differences of the output voltage of the detection coil at each frequency.

12. The calibration device for a non-destructive inspection/measurement system according to claim 9, wherein the calibration processing unit applies a combined signal comprising multiple sinusoids of mutually different frequencies to the excitation coil, and calibrates detection results in the detection processing unit by entering, as variables in simultaneous equations, the amplitudes and phase differences of the output voltage of the detection coil at each frequency.

13. The calibration device for a non-destructive inspection/measurement system according to claim 9, wherein the calibration processing unit applies to the excitation coil, as the sinusoidal signal or the combined signal, a burst signal having a leading section in which the amplitude gradually rises, a trailing section in which the amplitude gradually falls, and a measurement signal section, provided between the leading section and the trailing section, that is in the steady state and that is for data acquisition.

14. The calibration device for a non-destructive inspection/measurement system according to claim 9, wherein the calibration processing unit uses multi-variable simultaneous equations having five or more variables as the simultaneous equations.

15. The calibration device for a non-destructive inspection/measurement system according to claim 1, wherein the calibration processing unit applies to the excitation coil, as the sinusoidal signal or the combined signal, a burst signal having a leading section in which the amplitude gradually rises, a trailing section in which the amplitude gradually falls, and a measurement signal section, provided between the leading section and the trailing section, that is in the steady state and that is for data acquisition.

16. The calibration device for a non-destructive inspection/measurement system according to claim 1, wherein the calibration processing unit uses multi-variable simultaneous equations having five or more variables as the simultaneous equations.

17. A non-destructive inspection/measurement method using a calibration device for a non-destructive inspection/measurement system comprising an excitation coil and a detection coil, the excitation coil faces a test object body and excites the test object body, the detection coil faces the test object body and outputs a voltage in accordance with a magnetic field change generated in the test object body when the test object body is excited by the excitation coil, and a detection processing unit that applies, to the excitation coil for exciting the test object body, a sinusoidal signal or a combined signal comprising a plurality of sinusoids of mutually different frequencies, and that detects changes in the output voltage of the detection coil, the calibration device comprising a calibration processing unit that calibrates detection results in the detection processing unit by entering, as variables in simultaneous equations, amplitudes and phase differences of the output voltage of the detection coil at a plurality of calibration points of known thickness, on the test object body, and the calibration processing unit performing calibrations by using multiple different calibration conditions at each of the calibration points, and entering, into the simultaneous equations, the amplitudes and phase differences of output of the detection coil for each of the calibration conditions, the non-destructive inspection/measurement method comprises:

in the non-destructive inspection/measurement system, exciting the test object body by applying, to the excitation coil, the sinusoidal signal or the combined signal comprising multiple sinusoids having mutually different frequencies, with the excitation coil facing the test object body, and detecting the amplitude and the phase of the output voltage of the detection coil in accordance with magnetic field changes including magnetic flux due to eddy currents generated in the test object body; and the calibration processing unit calibrating the detection results in the detection processing unit by using multiple different calibration conditions, and entering, as variables in the simultaneous equations, the amplitudes and phase differences of the output voltage of the detection coil for each of the calibration conditions.

* * * * *